United States Patent
Selleck et al.

(10) Patent No.: US 11,053,501 B2
(45) Date of Patent: Jul. 6, 2021

(54) METHODS OF TREATING NEURODEGENERATIVE DISEASE BY INHIBITING N-DEACETYLASE N-SULFOTRANSFERASE

(71) Applicant: The Penn State Research Foundation, University Park, PA (US)

(72) Inventors: Scott Brian Selleck, Boalsburg, PA (US); Claire Reynolds-Peterson, Albany, NY (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 16/700,315

(22) Filed: Dec. 2, 2019

(65) Prior Publication Data

US 2020/0172910 A1    Jun. 4, 2020

Related U.S. Application Data

(60) Provisional application No. 62/773,557, filed on Nov. 30, 2018.

(51) Int. Cl.
*C12N 15/113* (2010.01)
*C12N 15/115* (2010.01)
*A61K 45/06* (2006.01)

(52) U.S. Cl.
CPC ........ *C12N 15/1137* (2013.01); *C12N 15/115* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2003/0109501 A1* | 6/2003 | Yang ........................ | C12Q 1/48 514/102 |
| 2003/0211562 A1* | 11/2003 | Bertozzi .................. | C12Q 1/48 435/15 |
| 2005/0042213 A1 | 2/2005 | Gelder et al. | |
| 2006/0292873 A1 | 12/2006 | Sasisekharan et al. | |
| 2009/0104627 A1* | 4/2009 | Yamamoto ........... | G01N 33/573 435/7.4 |
| 2010/0048638 A1 | 2/2010 | Crawford et al. | |
| 2011/0044975 A1 | 2/2011 | McEwan et al. | |
| 2011/0060029 A1* | 3/2011 | Iwatsubo ........... | A61K 31/7105 514/44 A |
| 2014/0302510 A1 | 10/2014 | Papy-Garcia et al. | |
| 2019/0151312 A1 | 5/2019 | Bhagwat et al. | |

OTHER PUBLICATIONS

Sheng et al. The Journal of Biological Chemistry 286 pp. 19768-19766 (Year: 2011).*
Deligney et al. The Journal of Biological Chemistry 285, 1701-1715 (Year: 2010).*
Garcia, B., The Role of Heparan Sulfate Proteoglycans in Bacterial Infection, Journal of Medical Microbiology & Diagnosis, 3:4, 2014.
Hansen, M. et al., Autophagy as a promoter of longevity: insights from model organisms, Nature Reviews in Molecular and Cellular Biology, Sep. 2018, 19(9):579-593.
Liu, C. et al., Neuronal heparin sulfates promote amyloid pathology by modulating brain amyloid-? clearance and aggregation in Alzheimer's disease, Science Translational Medicine, 8(332):332ra44, Mar. 30, 2016.
Reynolds-Petersen, Heparan sulfate proteoglycans regulate autophagy in *Drosophila*, Autophagy, Aug. 3, 2017; 13(8):1262-1279. Epub Apr. 12, 2017.

* cited by examiner

*Primary Examiner* — Brian Whiteman
(74) *Attorney, Agent, or Firm* — Julie K. Staple; Dinsmore & Shohl LLP

(57) ABSTRACT

A method of treating a subject suffering from a neurodegenerative disease characterized by insufficient autophagy is provided, the method comprising administering to the subject an effective amount of a composition that inhibits N-deacetylase N-sulfotransferase (NDST). Further provided is a method of identifying a modulator of autophagy.

15 Claims, 12 Drawing Sheets
Specification includes a Sequence Listing.

sfl parkin$^{\Delta 21}$ /mef2-Gal4 parkin$^1$   UAS-Atg5$^{RNAi}$; sfl parkin$^{\Delta 21}$ / mef2-Gal4 parkin$^1$

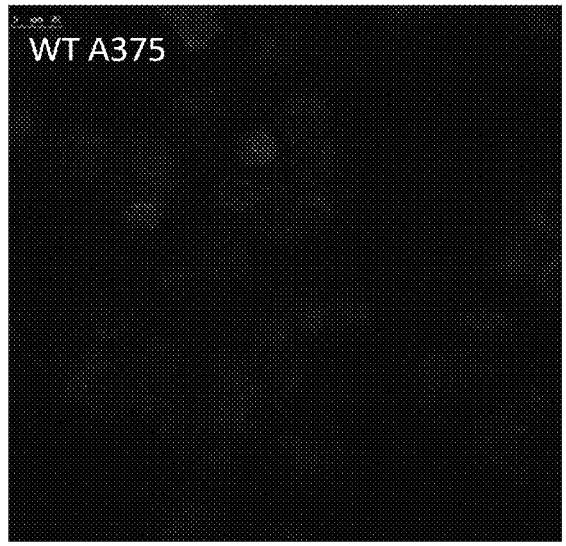
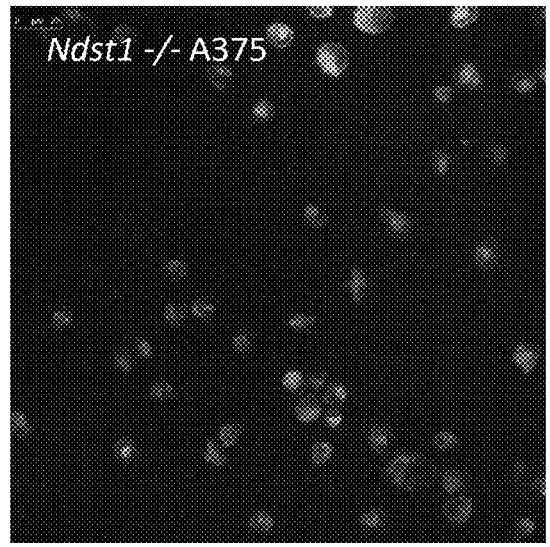
FIG. 13A    FIG. 13B
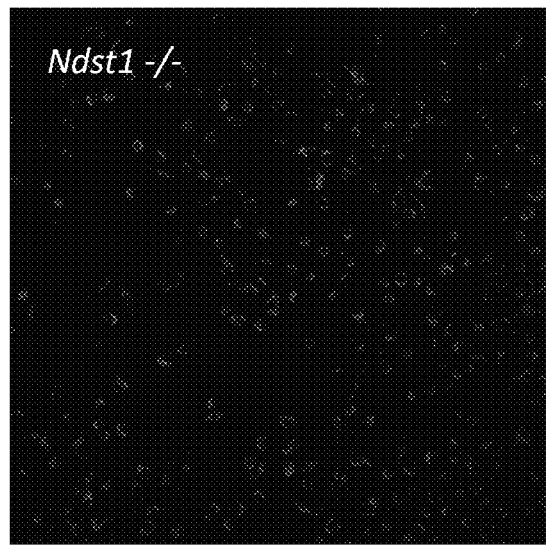
FIG. 14A    FIG. 14B

SEQUENCE LISTING

```
<160> NUMBER OF SEQ ID NOS: 1

<210> SEQ ID NO 1
<211> LENGTH: 556
<212> TYPE: PRT
<213> ORGANISM: Homo sapiens

<400> SEQUENCE: 1

Met Pro Ala Leu Ala Cys Leu Arg Arg Leu Cys Arg His Val Ser Pro
1               5                   10                  15

Gln Ala Val Leu Phe Leu Leu Gln Val Val Cys Gln Phe Ser Val Phe
            20                  25                  30

Ile Ser Ala Tyr Tyr Leu Tyr Gly Trp Lys Arg Gly Leu Glu Pro Ser
        35                  40                  45

Ala Asp Ala Pro Glu Pro Asp Cys Gly Asp Pro Pro Val Ala Pro
    50                  55                  60

Ser Arg Leu Leu Pro Leu Lys Pro Val Gln Ala Ala Thr Pro Ser Arg
65                  70                  75                  80

Thr Asp Pro Leu Val Leu Val Phe Val Glu Ser Leu Tyr Ser Gln Leu
                85                  90                  95

Gly Gln Glu Val Val Ala Ile Leu Glu Ser Ser Arg Phe Lys Tyr Arg
            100                 105                 110

Thr Glu Ile Ala Pro Gly Lys Gly Asp Met Pro Thr Leu Thr Asp Lys
        115                 120                 125

Gly Arg Gly Arg Phe Ala Leu Ile Ile Tyr Glu Asn Ile Leu Lys Tyr
    130                 135                 140

Val Asn Leu Asp Ala Trp Asn Arg Glu Leu Leu Asp Lys Tyr Cys Val
145                 150                 155                 160

Ala Tyr Gly Val Gly Ile Ile Gly Phe Phe Lys Ala Asn Glu Asn Ser
                165                 170                 175

Leu Leu Ser Ala Gln Leu Lys Gly Phe Pro Leu Phe Leu His Ser Asn
            180                 185                 190

Leu Gly Leu Lys Asp Cys Ser Ile Asn Pro Lys Ser Pro Leu Leu Tyr
        195                 200                 205
```

```
Val Thr Arg Pro Ser Glu Val Glu Lys Gly Val Leu Pro Gly Glu Asp
    210                 215                 220
Trp Thr Val Phe Gln Ser Asn His Ser Thr Tyr Glu Pro Val Leu Leu
225                 230                 235                 240
Ala Lys Thr Arg Ser Ser Glu Ser Ile Pro His Leu Gly Ala Asp Ala
                245                 250                 255
Gly Leu His Ala Ala Leu His Ala Thr Val Val Gln Asp Leu Gly Leu
            260                 265                 270
His Asp Gly Ile Gln Arg Val Leu Phe Gly Asn Asn Leu Asn Phe Trp
        275                 280                 285
Leu His Lys Leu Val Phe Val Asp Ala Val Ala Phe Leu Thr Gly Lys
    290                 295                 300
Arg Leu Ser Leu Pro Leu Asp Arg Tyr Ile Leu Val Asp Ile Asp Asp
305                 310                 315                 320
Ile Phe Val Gly Lys Glu Gly Thr Arg Met Lys Val Glu Asp Val Lys
                325                 330                 335
Ala Leu Phe Asp Thr Gln Asn Glu Leu Arg Ala His Ile Pro Asn Phe
            340                 345                 350
Thr Phe Asn Leu Gly Tyr Ser Gly Lys Phe Phe Gln Thr Gly Thr Asn
        355                 360                 365
Ala Glu Asp Ala Gly Asp Asp Leu Leu Leu Ser Tyr Val Lys Glu Phe
    370                 375                 380
Trp Trp Phe Pro His Met Trp Ser His Met Gln Pro His Leu Phe His
385                 390                 395                 400
Asn Gln Ser Val Leu Ala Glu Gln Met Ala Leu Asn Lys Lys Phe Ala
                405                 410                 415
Val Glu His Gly Ile Pro Thr Asp Met Gly Tyr Ala Val Ala Pro His
            420                 425                 430
His Ser Gly Val Tyr Pro Val His Val Gln Leu Tyr Glu Ala Trp Lys
        435                 440                 445
Gln Val Trp Ser Ile Arg Val Thr Ser Thr Glu Glu Tyr Pro His Leu
    450                 455                 460
Lys Pro Ala Arg Tyr Arg Arg Gly Phe Ile His Asn Gly Ile Met Val
465                 470                 475                 480
Leu Pro Arg Gln Thr Cys Gly Leu Phe Thr His Thr Ile Phe Tyr Asn
                485                 490                 495
Glu Tyr Pro Gly Gly Ser Ser Glu Leu Asp Lys Ile Ile Asn Gly Gly
            500                 505                 510
Glu Leu Phe Leu Thr Val Leu Leu Asn Pro Val Ser Ala Pro Gln Pro
        515                 520                 525
Met Ala Ala Gly Glu Lys Gly Leu Leu His Ser Leu Ser Ala Ala Asp
    530                 535                 540
Thr Gly Phe Leu Glu Pro Gly Lys Gly Gly Glu Ala
545                 550                 555
```

METHODS OF TREATING NEURODEGENERATIVE DISEASE BY INHIBITING N-DEACETYLASE N-SULFOTRANSFERASE

REFERENCE TO RELATED APPLICATION

This application claims priority to U.S. Provisional Application Ser. No. 62/773,557, filed Nov. 30, 2018, the entire content of which is incorporated herein by reference.

FIELD OF THE INVENTION

The present disclosure relates to the field of autophagy and the treatment of neurodegenerative diseases. More specifically, the present disclosure relates to methods of treating neurodegenerative diseases associated with autophagy by inhibiting the enzyme N-deacetylase N-sulfotransferase.

BACKGROUND OF THE INVENTION

Heparan sulfate modified proteins are abundant proteins of the cell surface and extracellular matrix, named for the unbranched and highly sulfated disaccharide polymers covalently attached to the protein core. Biosynthesis of heparan sulfate occurs in the golgi and mutations affecting this enzyme machinery compromise the modification of numerous proteins, including glypicans and syndecans, two integral membrane proteoglycans involved in signaling. Studies of genes encoding proteins required for heparan sulfate polymer synthesis and sulfation have been instrumental in defining the activities of heparan sulfate modified proteins. These genes are highly conserved across species, including *C. elegans*, *Drosophila*, mice, and humans. Heparan sulfate modified proteins are functionally diverse molecules, regulating growth factor signaling, endocytosis, and the distribution of molecules in the matrix. Both the protein core and the heparan sulfate chains govern these functions. The abundance and broad expression of heparan sulfate modified proteins, together with their diverse functions in modulating signaling, provide the capacity to effect cellular physiology in a myriad of ways, including autophagy.

Autophagy is important for proteostasis, organelle turnover, and protecting cells from a variety of cellular stresses. In vertebrates, basal autophagy is critical for normal cellular health, highlighted by the extensive neuronal death in the cerebrum and cerebellum of mice lacking Atg7, a critical autophagy component. Upregulation of constitutive autophagy increases lifespan in *C. elegans* and *Drosophila* and can rescue neurons from protein-aggregate toxicity in a number of models, including *Drosophila*. Recent work has demonstrated that increases in basal autophagy regulated by Beclin can also increase lifespan and health span in the mouse. There is also evidence that mitophagy, a component of autophagy, is important for removing damaged mitochondria and failure of mitochondrial surveillance has a significant role in the pathology of Parkinson's disease.

Previous studies have explored heparan sulfate and autophagy (Reynolds-Peterson, et al., Heparan sulfate proteoglycans regulate autophagy in *Drosophila*, Autophagy 13(8) 1262479 (2017)). The capacity of heparan sulfate modified proteins to suppress autophagy was also documented in fat body, a critical metabolic sensing and energy storage tissue in *Drosophila*. There are a number of findings in the mouse that indicate heparan sulfate modified protein-mediated inhibition of autophagy occurs in vertebrates as well. When heparan sulfate accumulates, such as in many lysosomal storage diseases, autophagy is suppressed. Transgene-mediated expression of a heparan sulfate-degrading enzymes, heparanase (Hpa1), increases autophagy, consistent with an inhibitory role of heparan sulfate modified proteins on autophagy. Conversely, gene knockout of Hpa1 results in suppression of autophagy in multiple tissues, consistent with an inhibitory role of heparan sulfate modified proteins on autophagy levels.

Specific heparan sulfate-modified proteins have been shown to affect autophagy distinct manners. Loss of Perlecan increases autophagy in mouse muscle, consistent with an autophagy-inhibitory activity. However, Endorepellin, a C-terminal fragment of Perlecan, and Decorin, a small leucine-rich proteoglycan, induce autophagy. These studies demonstrate that individual proteoglycans can either inhibit or stimulate autophagy in different cellular contexts.

Autophagy is required in all cell types for basic homeostasis and protects against cell death from stressors such as starvation, hypoxia, reactive oxidant exposure, and acute protein misfolding due to disruption of the endoplasmic reticulum. While this cellular recycling pathway is broadly important for survival, certain tissues and cell types are more sensitive to its loss. The central nervous system is one such tissue in which blockage of autophagy carries an invariably heavy toll. Inhibition of autophagy results directly in neuronal death and the development of neurodegenerative disease in mice. This is likely due to the structural and energetic sensitivity of neurons.

Axons and dendrites require an array of specialized proteins to function and the constant vesicular trafficking required for synaptic transmission consumes a great deal of energy. Furthermore, the need for specialized proteins and ATP is located at sites distal from the cell body. This need is met by localization of mitochondria and protein translation to the axons and dendrites. Appropriate mitochondrial turnover is particularly important in neurons, which, as post-mitotic cells, cannot dilute the accumulation of detective organdies through cell division.

The long, thin axonal structure is also highly sensitive to disruption when autophagic degradation is compromised. Failure of autophagy leads to disruption of microtubule-dependent transport in the axon, which causes accumulation of p62- and ubiquitin-positive aggregates in focal swellings along the length of the axon. Axonal focal swelling is a pathological hallmark of both Alzheimer's disease and Parkinson's disease. Changes in axonal width and membrane quality caused by axonal focal swelling compromise the propagation of action potentials along the membrane, slowing and even completely blocking their transmission.

Autophagy is a critical homeostatic process, without which cells succumb to oxidative stress generated by damaged mitochondria and the accumulation of autophagic substrates. While proteasomal degradation is thought to be unregulated in response to autophagic suppression, this redundancy can only assist in the clearance of substrates that the proteasome is physically capable of degrading, which limits its ability to adjust for autophagic failure over long periods of time. In no tissue is this effect more evident than the central nervous system. Failure of autophagy is associated with neuronal death in both Parkinson's disease (PD) and Alzheimer's disease (AD).

Autophagy in the central nervous system performs critical functions in development and neuronal survival. Dysregulation of neuronal autophagy is associated with neurodegenerative diseases and aging, as well as abnormal synaptic features observed in neurodevelopmental disorders.

The effects of heparan sulfate modified proteins on autophagy regulation, particularly with respect to treatment of pathological conditions associated with autophagy, are not yet fully understood. There is a continuing need for methods of treating such pathological conditions, including neurodegenerative diseases, in a subject in need thereof.

SUMMARY OF THE INVENTION

The present disclosure elucidates the effects of heparan sulfate biosynthesis levels and sulfation state on known physiological functions of autophagy. The disclosure shows that decreasing heparan sulfate levels or sulfation has all the hallmarks of global activation of basal autophagy, increasing resistance to oxidative stress and extending lifespan. The disclosure also demonstrates the capacity of altered heparan sulfate biosynthesis to provide protection from cell loss in a Presenilin model of Alzheimer's Disease (AD), or deficits in mitochondrial, surveillance mediated by mutations in parkin, the homolog of PARK2. In both of these models of human neurodegenerative disorders, inhibiting heparan sulfate biosynthesis enzyme N-deacetylase N-sulfotransferase (NDST) rescued cell loss, showing that changes in NDST can affect the capacity of cells to tolerate a variety of cellular stresses.

Accordingly, in one aspect, a method of treating a subject suffering from a neurodegenerative disease characterized by insufficient autophagy is provided, the method comprising administering to the subject an effective amount of a composition that inhibits N-deacetylase N-sulfotransferase (NDST). Neurodegenerative diseases characterized by insufficient autophagy include, but are not limited to Alzheimer's disease, Parkinson's disease, Huntington's disease, amyotrophic lateral sclerosis (ALS), and priori encephalopathies.

In another aspect, a method of identifying, a modulator of autophagy is provided, the method comprising contacting an NDST polypeptide, a substrate for NDST, and a test substance under reaction conditions that promote specific interaction between the NDST polypeptide and the substrate for NDST, and detecting a change in specific interaction between the NDST polypeptide and the substrate for NDST.

In another aspect, a method of identifying a modulator of autophagy is provided, the method comprising contacting an NDST polypeptide, a substrate for NDST, and a test substance under reaction conditions that promote specific interaction between the NDST polypeptide and the substrate for NDST, and detecting a change in enzymatic activity of the NDST. According to particular aspects, the detected change in enzymatic activity of the NDST is a change in deacetylation of the substrate and/or a change in sulfation of the substrate. The substrate may be N-acetylglucosamine (GlcNAc). Thus, in one aspect, a method of identifying a modulator of autophagy is provided, the method comprising contacting an NDST polypeptide, a substrate for NDST wherein the substrate is GlcNAc, and a test substance under reaction conditions that promote specific interaction between the NDST polypeptide and the GlcNAc, and detecting a change in enzymatic activity of the NDST on the GlcNAc, wherein the detected change in enzymatic activity of the NDST is a change in deacetylation of the substrate and/or a change in sulfation of the substrate.

These and other objects, features, embodiments, and advantages will become apparent to those of ordinary skill in Me art from a reading of the following detailed description and the appended claims.

BRIEF DESCRIPTION OF THE DRAWINGS

FIG. 5A is an image showing a retina from a control animal.

FIG. 5B is an image showing a retina from an animal that expresses presenilin and showing that expression of Presenilin (elav-Gal4c155>UAS-Psn) produces a rough and reduced retina, compared with the control in FIG. 5A, as well as disruption of the arrangement of ommatidia.

FIG. 5C is an image showing a retina from an animal that expresses presenilin and RNAi directed to ttv and illustrating that RNAi of ttv suppressed the effects of Presenilin overexpression on retinal size to a significant degree (compare FIG. 5B to FIG. 5C and see measurements, FIG. 5E).

FIG. 5D is an image showing a retina from an animal that expresses presenilin and RNAi directed to sfl and illustrating that RNAi of sfl suppressed the effects of Presenilin overexpression on retinal size to a significant degree (compare FIG. 5B to FIG. 5D and see measurements. FIG. 5E).

FIG. 5E is a scatter plot illustrating that the area, of the retinas from control animals, UAS-PSn animals, UAS-Psn; UAS-sflRNAi animals and UAS-Psn; UAS-ttvRNAi animals was determined to provide a measure of cell loss; data is presented as a scatter plot of each animal with the mean plus/minus 95% confidence interval. *(top row) indicate comparison to control, while + (bottom row) indicate comparison to Presenilin expression alone. */+$p<0.05$, $p<0.01$, */+++$p<0.001$, *$p<0.0001$.

FIG. 5F is a scatter plot illustrating results of a computational method (Flynotyper) used to obtain a measure of retinal disorganization, with higher scores representing increased disarray. Only sfl RNAi significantly rescued the disordering of the retina, measured by Flynotyper morphological scoring parameters; data is presented as a scatter plot of each animal with the mean plus/minus 95% confidence interval. *(top row) indicate comparison to control, while + (bottom row) indicate comparison to Presenilin expression alone. */+$p<0.05$, /++$p<0.01$, */+++$p<0.001$, ****$p<0.0001$. Statistical testing utilized Kruskal-Wallis non-parametric group test followed by Dunn's pairwise comparisons.

FIG. 6A is an image showing a low magnification confocal view of the indirect flight muscles of an adult control fly, stained with anti-ubiquitin antibody.

FIG. 6A' is an image showing phalloidin staining of actin filaments from animals of the same genotype as in FIG. 6A.

FIG. 6B is an image showing, a low magnification confocal view of the indirect flight muscles of an adult parkΔ21/park1 fly, stained with anti-ubiquitin antibody.

FIG. 6B' is an image showing phalloidin staining of actin filaments from animals of the same genotype as in FIG. 6B.

FIG. 6C is an image showing a low magnification confocal view of the indirect flight muscles of an adult sfl parkΔ21/park1 fly, stained with anti-ubiquitin antibody.

FIG. 6C' is an image showing phalloidin staining of actin filaments from animals the same genotype as in FIG. 6C.

FIG. 6D is a graph showing flight assay results of control (park1/f), park mutants, and park mutants bearing sfl alleles (error bars showing standard error). Heterozygosity for sfl significantly rescues flight capability measured by this assay, from essentially no flight, to nearly wild type levels.

FIG. 7A is an image showing ubiquitin in adult flight muscles from parkΔ21/+ animals.

FIG. 7B is an image showing ubiquitin in adult flight muscles from parkΔ21/park1 animals.

FIG. 7C is an image showing ubiquitin in adult flight muscles from ttv parkΔ21/park1 animals.

FIG. 8A is an image of a wild type genotype control animal.

FIG. 8B is an image of a parkΔ21/park1 mutant animal.

FIG. 8C is an image of a sfl parkΔ21/park1 mutant animal.

FIG. 9A shows confocal images of adult flight muscles stained with anti-ubiquitin antibody from sfl parkΔ21/mef2-Gal4 park1 animals. mef2-Gal4 provides muscle-specific expression of the UAS-Atg5 RNAi transgene.

FIG. 9B shows confocal images of adult flight muscles stained with anti-ubiquitin antibody from sfl parkΔ21/mef2-Gal4 park1 bearing a UAS-Atg5 RNAi transgene. mef2-Gal4 provides muscle-specific expression of the UAS-Atg5 RNAi transgene.

FIG. 13A is an image that shows LysoTracker and Cyto-ID staining of lysosomes and autophagosomes in wild-type (WT) human A375 melanoma cells;

FIG. 13B is an image that shows LysoTracker and Cyto-ID staining of lysosomes and autophagosomes in CRISPR-mediated knockout of Ndst1 (Ndst1-/-) in human A375 melanoma cells results in elevated levels of autophagosomes and lysosomes under baseline conditions (rich growth media).

FIG. 14A is an image that shows the Cyto-ID marker for autophagosomes in wild-type (WT) human A375 cells after autophagy induction with rapamycin and arrest of lysosome maturation with chloroquine;

FIG. 14B, is an image that shows the Cyto-ID marker for autophagosomes in human Ndst1$^{-/-}$ A375 cells after autophagy induction with rapamycin and arrest of lysosome maturation with chloroquine. Comparison of FIG. 14A with FIG. 14B shows that this process increases the number of autophagosomes by inhibiting their fusion with lysosomes. Human Ndst1$^{-/-}$ A375 cells show an elevated level of autophagosome accumulation;

DETAILED DESCRIPTION OF THE INVENTION

Figure 1:
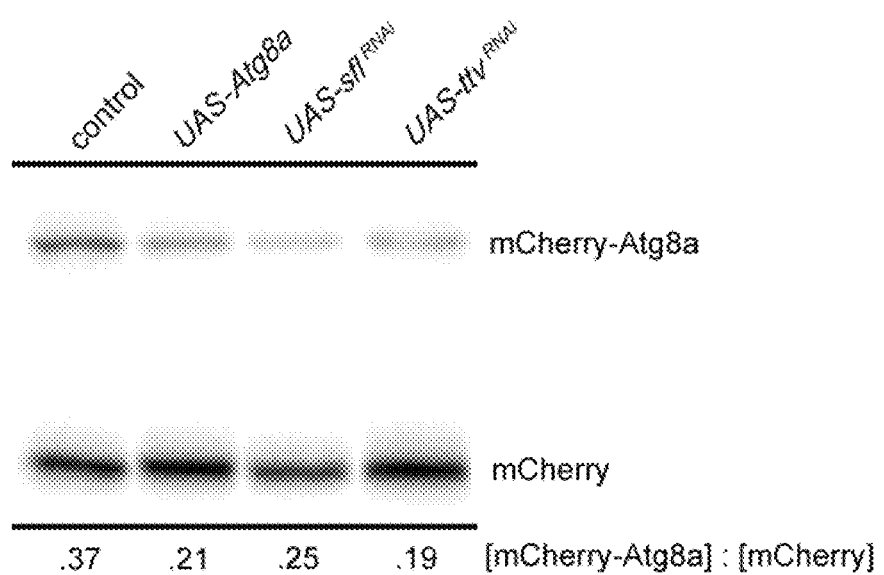
FIG. 1 is an image of a Western blot showing autophagy-dependent cleavage of mCherry-Atg8a is increased in the CNS upon RNA interference of sfl or ttv. Heads from adult animals bearing transgene constructs expressing an mCherry-Atg8a fusion protein in neurons were obtained and mCherry-Atg8a protein detected by SDS-PAGE and western blotting with anti-mCherry antibody. The large fusion protein is cleaved during autophagosome maturation to a relatively stable product that contains the mCherry epitope. The ratio of the parental and cleavage products provides a measure of autophagy-dependent activity in the CNS. Activation of autophagy in neurons with overexpression of Atg8a shows increased relative levels of the mCherry-bearing cleavage product. Knockdown of either sfl or ttv using RNAi also produces an increase in the relative levels of mCherry-Atg8a cleavage in the brain. QPCR of sfl mRNA showed reductions to 42% of wild type levels.

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; Remington: The Science and Practice of Pharmacy, Lippincott Williams & Wilkins, 21st Ed., 2005 L. V. Allen, Jr. et al., Ansel's Pharmaceutical Dosage Forms and Drug Delivery Systems, 8th Ed, Philadelphia, Pa.: Lippincott. Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

The terms "modulating" and "modulation" refer to an increase or decrease.

The terms "treat," "treatment," and "treating," as used herein, refer to a method of preventing, inhibiting progression, and/or alleviating or abrogating a disease, disorder, and/or symptoms thereof in a subject.

The term "subject" refers to an individual in need of treatment. While the present invention describes compositions and methods for treatment of human subjects in need thereof, the present invention is not limited to human subjects and the term subject generally includes mammals and birds, such as, but not limited to, non-human primates, cats, dogs, cows, horses, rodents, pigs, sheep, goats and poultry.

Autophagy is a regulated cellular pathway involved in degradation of cellular components. Regulation of autophagy is complex and includes transcriptional, post-transcriptional and post-translational mechanisms. Target of Rapamycin (TOR) is a master regulator of autophagy, affecting both the activity of key Atg gene transcription factors as well as the activity of autophagosome assembly proteins. Tor activity serves to suppress autophagy and growth conditions that favor Tor activation result in reduced levels of autophagic flux. Heparan sulfate modified proteins play critical roles in signaling pathways that lead to Tor activation via PI3 kinase and this is one potential mechanism of heparan sulfate-mediated regulation of autophagy.

This disclosure evidences the broad inhibitory effect of heparan sulfate modification ort autophagy in Drosophila. Studies in mice indicate this regulatory relationship is represented in vertebrates as well. Heparanase (Hpa) is an endo-D-glucuronidase that cleaves heparan sulfate and transgenic mice with ectopic expression of Hpa exhibit increased autophagy levels in multiple tissues. Conversely, knockouts of Hpa results in autophagic suppression. Collectively, these findings indicate heparan sulfate modified protein suppression of autophagy is evolutionarily conserved and occurs in many cell types and tissues.

The capacity of autophagy to remove protein aggregates and damaged mitochondria provides a means of protecting cells against pathological events that lead to cell death. Activation of autophagy is thus protective for neurodegeneration and conversely, suppression of autophagy confers susceptibility to cell loss. Interestingly, lysosomal storage disorders, where deficits in certain degradative enzymes result in accumulation of heparan sulfate, produce suppression of autophagy and neuronal loss. A number of human neurodegenerative disorders, including Alzheimer's disease (AD), Huntington's disease, and Amyotrophic Lateral Sclerosis (ALS), show protein aggregation and accumulation. Deficits in mitochondrial turnover and clearance are also implicated in neurodegeneration, Parkinson's disease being a well-studied, case in point. The data presented herein demonstrate that modulation of heparan sulfate synthesis by modulating NDST has the capacity to rescue cell loss in two models of human neurodegenerative diseases, one mediated by overexpression of Presenilin and the other by loss of parkin function. Overexpression of Presenilin phenocopies loss-of-function mutants in Drosophila, indicating this model works via a dominant-negative mechanism. Given that the majority of human AD pathogenic mutations affecting PSEN1 reduce or eliminate γ-secretase function, the fly model provides a reasonable assay for Presenilin-mediated pathology.

Data described herein show that reducing heparan sulfate biosynthetic capacity can rescue cell pathology produced by reductions of parkin function. Parkin, the fly homolog of PARK2, participates in mitochondrial surveillance via the ubiquitin-modification of outer membrane proteins, tagging, them for mitophagy and degradation in the lysosome. Presently disclosed data show that reducing heparan sulfate can suppress the muscle abnormalities in parkin mutants, including the restoration of mitochondrial morphology, and indicates that deficits in mitochondrial surveillance can be rescued by increasing autophagy. The data indicates that heparan sulfate biosynthesis is a useful target for intervention to increase autophagy and mitophagy, providing some protection in a variety of neurodegenerative disorders.

Methods of modulating autophagy to treat a condition or disease in a subject in need thereof are provided according to aspects of the present invention which include: administering a composition effective to decrease expression levels and/or activity of heparan sulfate in the subject, thereby increasing autophagy and treating the condition or disease in the subject. According to aspects of the present invention, the composition is an anti-heparan sulfate composition effective to decrease expression levels and/or activity of heparan sulfate in the subject, thereby increasing autophagy and treating the condition or disease in the subject.

In embodiments, the composition is a specific inhibitor of a heparan sulfate synthesis enzyme. In aspects, heparan sulfate synthesis enzymes include, but are not limited to, inhibitors of chain initiation, inhibitors of chain elongation, inhibitors of chain modification, inhibitors of N-deacetylation/N-sulfation, inhibitors of sulfation such as inhibitors of 2-O-sulfation, 3-O-sulfation, or 6-O-sulation. In aspects, heparan sulfate synthesis enzymes include, but are not limited to, exostosin 1, or N-deacetylase N-sulfotransferase.

According to aspects of the present invention, a method of modulating autophagy to treat a condition or disease in a subject in need thereof is provided, the method comprising administering a composition effective to inhibit N-deacetylase N-sulfotransferase in the subject, thereby modulating autophagy and treating the condition or disease in the subject.

According to aspects of the present invention, a method of modulating autophagy to treat a condition or disease in a subject in need thereof is provided, the method comprising administering a composition effective to inhibit exostosin 1 in the subject, thereby modulating autophagy and treating the condition or disease in the subject.

According to aspects of the present mention a method of modulating autophagy to treat a condition or disease in a subject in need thereof is provided, the method comprising administering a composition effective to inhibit N-deacetylase N-sulfotransferase in the subject, thereby modulating autophagy and treating the condition or disease in the subject.

NDST is a bifunctional enzyme that converts N-acetylglucosamine (GlcNAc) residues to N-sulfo glucosamine (GlcNS)) residues. The N-deacetylase domain removes the acetyl group from GlcNAc to form N-unsubstituted glucosamine (GlcNH2), whereas the N-sulfotransferase domain transfers a sulfo group to the GlcNH2 residues to form GlcNS. The NDST modification step is essential for the biosynthesis of heparan sulfate, as other heparan sulfate biosynthetic enzymes, such as C5 epimerase, 2-O-sulfotransferase, and 3-O-sulfotransferase, all require the presence of GlcNS residues to complete their modifications.

According to aspects of the invention, the composition is an anti-N-deacetylase N-sulfotransferase (NDST) composition effective to decrease expression levels and/or activity of heparan sulfate and/or NDST in the subject, thereby increasing autophagy and treating the condition or disease in the subject.

According to aspects of the invention, the composition is an anti-N-deacetylase N-sulfotransferase (NDST) composition effective to decrease expression levels and/or activity of NDST and heparan sulfate in the subject, thereby increasing autophagy and treating the condition or disease in the subject.

Autophagy can be detected and/or monitored according, to standard methodology, for example, as described in Klionsky, J., et al., 2016, Guidelines for the use and interpretation of assays for monitoring autophagy (3rd edition), Autophagy, 12:1-222.

According to aspects of the present invention, the disease to be treated in a subject in need thereof is a neurodegenerative disease. According to aspects of the present invention, the neurodegenerative disease is characterized by an intracellular defect, such as, but not limited to, intracellular protein aggregates and increased levels of intracellular reactive oxygen species.

According to aspects of the present invention, the neurodegenerative disease is a disease characterized by an intracellular defect, the disease including but not limited to Alzheimer's disease, Parkinson's disease, Huntington's disease, amyotrophic lateral sclerosis, or a prion encephalopathy. In embodiments, prion encephalopathies include, but are not limited to, spongiform encephalopathies such as Creutzfeld-Jakob disease, kuru, and mad cow disease.

Thus, administration of an anti-NDST composition effective to decrease expression levels and/or activity of heparan sulfate and NDST to a subject is effective to treat a neurodegenerative disease characterized by an intracellular defect in a subject.

According to aspects of the present invention, the neurodegenerative disease to be treated is Alzheimer's disease and the intracellular protein aggregates comprise intracellular aggregates of tau, which accumulate in neurons of individuals with Alzheimer's disease. Thus, administration of an anti-N-deacetylase N-sulfotransferase composition effective to decrease expression levels and/or activity of heparan sulfate and NDST to a subject is effective to treat Alzheimer's disease in a subject.

According to aspects of the present invention, the neurodegenerative disease to be treated is Alzheimer's disease and the intracellular protein aggregates comprise intracellular aggregates of tau, which accumulate in neurons of individuals with Alzheimer's disease. Thus, administration of an anti-N-deacetylase N-sulfotransferase composition effective to decrease expression levels and/or activity of heparan sulfate and NDST in a subject is effective to treat Alzheimer's disease in a subject.

In embodiments, the anti-NDST composition can be a nucleic acid, a protein, carbohydrate, a lipid, a small molecule organic or inorganic anti-NDST composition, or a combination of any two or more thereof.

In particular aspects, an anti-NDST composition effective to decrease expression levels and/or activity of NDST in the skin of the subject is formulated for topical application.

A topical formulation can be an ointment, lotion, cream or gel in particular aspects. Topical dosage forms such as ointment, lotion, cream or gel bases are described in Remington: The Science and Practice of Pharmacy, 21st Ed., Lippincott Williams & Wilkins, 2006, p. 880-882 and p. 886-888; and in Allen, L. V, et al., Ansel's Pharmaceutical Dosage Forms and Drug Delivery Systems, 8th Ed., Lippincott Williams & Wilkins, 2005, p. 277-297.

Thus, according to aspects of the present invention, an anti-heparan sulfate composition is a nucleic acid which is a specific inhibitor of exostosin 1, or a specific inhibitor of NDST, selected from the group consisting of: an antisense molecule, an aptamer, an RNA interference nucleic acid, such as, but not limited to, siRNA, shRNA, or microRNA; or a catalytic nucleic acid, such as, but not limited to, a DNAzyme, or a ribozyme.

An anti-NDST composition which is a nucleic acid can be produced by chemical synthesis and/or using molecular biology techniques known in the art. For example, chemical synthesis of oligonucleotides is described in Herdewijn, P. (Ed.), Oligonucleotide Synthesis: Methods and Applications, Methods in Molecular Biology, Humana Press, 2004. Molecular biology methods relating to anti-heparan sulfate composition nucleic acid synthesis are described, for example, in Sambrook, J. and Russell, D. W., Molecular Cloning: A Laboratory Manual, Cold Spring Harbor Laboratory Press, 3rd Ed, 2001; and Engelke, D. R., RNA Interference (RNAi): Nuts and Bolts of RNAi Technology, DNA Press LLC, Eagleville, Pa., 2003. Naturally occurring or modified nucleotides may be used in constructing an anti-N-deacetylase N-sulfotransferase composition which is a nucleic acid. Modified nucleotides may be used to increase the stability of an anti-N-deacetylase N-sulfotransferase nucleic acid composition, increase resistance to nucleases, or enhance stability of binding to a target, for instance. Examples of modified nucleotides include phosphorothioates, phosphorodithioates boronophosphates, alkyl phosphonates such as methyl phosphonates, and phosphoramidates such as 3'-amino phosphoramidates.

Generally, antisense nucleic acids useful for expression of a target are in the range of about 12 to about 100 nucleotides in length, or longer.

In one embodiment, an anti-NDST composition is a double-stranded RNA molecule that inhibits expression of a target gene, such as an enzyme required for heparan sulfate synthesis, by RNA interference.

RNA interference is a target sequence-specific method of inhibiting a selected gene. RNA interference has been characterized in numerous organisms and is known to be mediated by a double-stranded RNA, also termed herein a double-stranded RNA compound. Briefly described, RNA interference involves a mechanism triggered by the presence of small interfering RNA, siRNA, resulting in degradation of a target complementary mRNA, siRNA is double-stranded. RNA which includes a nucleic acid sequence complementary to a target sequence in the gene to be silenced. The double-stranded RNA may be provided as a long double-stranded RNA compound, in which case it is subject to cleavage by the endogenous endonuclease Dicer in a cell. Cleavage by Dicer results in siRNA duplexes having about 21-23 complementary nucleotides in each of the sense strand and the antisense strand, and optionally 1-2 nucleotide 3' overhangs on each of the two strands.

Alternatively, siRNA is provided as a duplex nucleic acid having a sense strand and an antisense strand, wherein the sense and antisense strands are substantially complementary and each of the sense and antisense strands have about 16-30 nucleotides. The complementary sense and antisense strands and optionally include 1-2 nucleotide 3' overhangs on one or both of the two strands. In one embodiment, an siRNA is preferred which has sense and antisense strands, wherein each of the two strands has 21-23 nucleotides, wherein 2 nucleotides on the 3' end of each strand are overhanging and the remaining 19-21 nucleotides are 100% complementary. As noted above, further details of siRNA compounds are described in Engelke, D. R., RNA Interference (RNAi): Nuts and Bolts of RNAi Technology, DNA Press LLC, Eagleville, Pa., 2003 Additional description of siRNA length and composition is found in Elbashir, S. M. et al., Genes and Devel., 15:188-200, 2001; and O'Toole, A. S. et al., RNA, 11:512-516, 2005.

siRNA provided as a duplex nucleic acid having a sense strand and an antisense strand may be configured such that the sense strand and antisense strand form a duplex in hybridization conditions but are otherwise unconnected. A double-stranded siRNA compound may be assembled from separate antisense and sense strands. Thus, for example, complementary sense and antisense strands are chemically synthesized and subsequently annealed by hybridization to produce a synthetic double-stranded siRNA compound.

Further, the sense and antisense strands for inclusion in siRNA may be produced from one or more expression cassettes encoding the sense and antisense strands. Where the sense and antisense strands are encoded by a single expression cassette, they may be excised from a produced transcript to produce separated sense and antisense strands and then hybridized to form a duplex siRNA. See, for example, Engelke, D. R, RNA Interference (RNAi): Nuts and Bolts of RNAi Technology, particularly chapters 5 and 6, DNA Press LLC, Eagleville, Pa., 2003 for further details of synthetic and recombinant methods of producing siRNA.

In a further alternative, a double-stranded "short hairpin" RNA compound, termed "shRNA" or "hairpin siRNA" includes an antisense strand and a sense strand connected by a linker, shRNA may be chemically synthesized or formed by transcription of a single-stranded RNA from an expression cassette in a recombinant nucleic acid construct. The shRNA has complementary regions which form a duplex under hybridization conditions, forming a "hairpin" conformation wherein the complementary sense and antisense strands are linked, such as by a nucleotide sequence of about 1-20 nucleotides. In general, each of the complementary sense and antisense strands have about 16-30 nucleotides.

As noted, siRNA and shRNA may be expressed from a double-stranded DNA template encoding the desired transcript or transcripts. A double-stranded DNA template encoding the desired transcript or transcripts is inserted in a vector, such as a plasmid or viral vector, and operably linked to a promoter for expression in vitro or in vivo. Plasmids and viral vectors suitable for transcription of a double-stranded DNA template are known in the art. Particular viral vectors illustratively include those derived from adenovirus, adeno-associated virus and lentivirus.

An anti-NDST composition for inhibition of NDST may be an antibody according to aspects of the present invention. An anti-NDST antibody inhibits heparan sulfate indirectly, such as by specific binding to heparan sulfate synthesis enzyme NDST.

The term "antibody" is used herein in its broadest sense and includes single antibodies and mixtures of antibodies characterized by substantially specific binding to an antigen. An antibody provided according to compositions and methods is illustratively a polyclonal antibody, a monoclonal antibody, a chimeric antibody, a humanized antibody, and/or an antigen binding antibody fragment, for example. The term antibody refers to a standard intact immunoglobulin having four polypeptide chains including two heavy chains (H) and two light chains (L) linked by disulfide bonds in particular embodiments. Antigen binding antibody fragments illustratively include an Fab fragment, an Fab' fragment, an F(ab')2 fragment, an Fd fragment, an Fv fragment, an scFv fragment and a domain antibody (dAb), for example. In addition, the term antibody refers to antibodies of various classes including IgG, IgM, IgA, IgD and IgE, as well as subclasses, illustratively including for example human subclasses IgG1, IgG2, IgG3 and IgG4 and marine subclasses IgG1, IgG2, IgG2a. IgG2b, IgG3 and IgGM, for example.

Antibodies, antigen-binding fragments and methods for their generation are known in the art, for instance, as described in Antibody Engineering, Kontemann, R. and Dübel, S. (Eds.), Springer, 2001; Harlow, E. and Lane, D., Antibodies: A Laboratory Manual, Cold Spring Harbor Laboratory Press, 1988; Ausubel. F. et al., (Eds.), Short Protocols in Molecular Biology, Wiley, 2002; J. D. Pound (Ed.) immunochemical Protocols, Methods in Molecular Biology, Humana Press, 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975).

The term "aptamer" refers to a nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Techniques for identification and generation of aptamers is known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

An anti-NDST composition is a "decoy" agent according to aspects of the present invention. The term "decoy agent" as used herein refers to an agent which specifically interacts with NDST and thereby inhibits normal physiological functions of heparan sulfate and/or NDST. An example of a heparan sulfate decoy agent is a xyloside.

Pharmaceutical compositions including a composition effective to modulate expression levels and/or activity of heparan sulfate and NDST and a pharmaceutically acceptable carrier in particular aspects of the present invention.

The term "pharmaceutically acceptable carrier" refers to a carrier which is substantially non-toxic to a subject to which the composition is administered and which is substantially chemically inert with respect to the active component or components. Pharmaceutically acceptable carriers and formulation of pharmaceutical compositions are known in the art, illustratively including, but not limited to, as described in Remington: The Science and Practice of Pharmacy, 21st Ed., Lippincott, Williams & Wilkins, Philadelphia, Pa., 2006; and Allen, L. V. et al., Ansel's Pharmaceutical Dosage Forms and Drug Delivery Systems, 8th Ed., Lippincott, Williams & Philadelphia, Pa., 2005.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about bye the use of agents delaying absorption, for example, aluminum monostearate and gelatin.

Solid dosage forms for oral administration include capsules, tablets, pills, powders, and granules. In such solid dosage forms, a therapeutic composition is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to a composition effective to modulate levels and/or activity of heparan sulfate, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

A pharmaceutical composition includes a liposomal formulation of a composition effective to modulate expression levels and/or activity of heparan sulfate or N-deacetylase N-sulfotransferase in particular aspects of the present invention.

Liposomal formulations according to aspects of the present invention include can include one or more types of neutral, cationic lipid and/or anionic lipid, such that the liposomal formulations have a net neutral surface charge at physiological pH. According to aspects, a PEG-modified lipid is included.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003 L. V. Allen, Jr. et al., Ansel's Pharmaceutical Dosage Forms and Drug Delivery Systems, 8th Ed., Philadelphia, Pa.: Lippincott, Williams & Wilkins, 2005, pp. 663-666; and A. R. Gernnaro, Remington: The Science and Practice of Pharmacy, Lippincott Williams & Wilkins, 21st ed., 2005, pp. 766-767.

A composition effective to modulate expression levels and/or activity of heparan sulfate and/or NDST may be administered to a subject by any of a variety of systemic and/or local routes according to aspects of methods of the present invention including, but not limited to, intravenous, intramuscular, subcutaneous, intraperitoneal, oral, otic, rectal, vaginal, topical, parenteral, pulmonary, ocular, nasal, intratumoral and mucosal.

A composition effective to modulate levels and/or activity of heparan sulfate and/or NDST may be administered acutely or chronically according to aspects of methods of the present invention.

A therapeutically effective amount of a composition effective to modulate expression levels and/or activity of heparan sulfate and/or NDST according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. Further, dosage may be adjusted depending on whether treatment is to be acute or continuing.

An additional therapeutic agent may be administered in addition to a composition effective to modulate levels and/or activity of heparan sulfate and/or NDST. Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, anti-inflammatory agents, anxiolytics, chemotherapeutic agents, diuretics, growth factors, hormones, non-steroidal anti-inflammatory agents, steroids and vasoactive agents.

Additional therapeutic agents included in aspects of methods and compositions of the present invention include, but are not limited to, an anti-Alzheimer's agent, such as a cholinesterase inhibitor, such as donepezil, galantamine, memantine, rivastigmine, and a combination of two or more thereof. Additional therapeutic agents included in aspects of methods and compositions of the present invention include, but are not limited to, an anti-Alzheimer's agent, such as an anti-beta amyloid agent, such as BAN2401.

Additional therapeutic agents included in aspects of methods and compositions of the present invention include, but are not limited to, an anti-Parkinsons disease agent, such as a dopamine precursor, such as levodopa and carbidopa; a dopamine agonist, such as pramipexole, ropinirole, rotigotine, and apomorphine; an MAO B inhibitor, such as selegiline, rasagiline, and safinamide; a catechol O-methyltransferase (COMT) inhibitor such as entacapone and tolcapone; an anticholinergic such as benztropine and trihexyphenidyl; and a combination of two or more thereof.

Additional therapeutic agents included in aspects of methods and compositions of the present invention include, but are not limited to, an anti-Huntington's disease agent, such as a motor symptom inhibitor, such a xenazine, risperidone, haloperidol, chlorpromazine, and a benzodiazepine; an antidepressant, such as a selective serotonin re-uptake inhibitor; an antipsychotic such as quetiapine, risperidone, and olanzapine; a mood stabilizer such as valproate, carbamazepine, and lamotrigine; and a combination of two or more thereof.

Additional therapeutic agents included in aspects of methods and compositions of the present invention include, but are not limited to, an anti-ALS agent, such as an anti-excitotoxic agent, such as riluzole, talampunci, ceftriaxone, gacyclidine, valproate, and lithium; a mitochondrial protectant such as olesoxime, GNX-4728, and trehalose; an anti-apoptotic agent, such as dasatinib, erythropoietin; an anti-oxidative agent such as bromocriptine, resveratrol, and WN1316; an antiimflammatory agent such as TNF-alpha; a neurotrophic factor such as GDNF; and a combination of two or more thereof.

Additional therapeutic agents included in aspects of methods and compositions of the present invention include, but are not limited to, an anti-prion disease agent, such as a motor symptom inhibitor, such as xenazine, risperidone, haloperidol, chlorpromazine, and a benzodiazepine; an antidepressant, such as a selective serotonin re-uptake inhibitor; an antipsychotic such as quetiapine, risperidone, and olanzapine; a mood stabilizer such as valproate, carbamazepine, and lamotrigine; and a combination of two or more thereof.

Methods of modulating autophagy to treat an undesirable skin condition or skin disease in a subject in need thereof are provided according to aspects of the present invention which include: administering an anti-heparan sulfate composition effective to decrease expression levels and/or activity of heparan sulfate in the skin of the subject, thereby increasing autophagy and treating the skin condition or skin disease in the subject. According to aspects of methods of modulating autophagy to treat an undesirable skin condition or skin disease in a subject an anti-heparan sulfate composition effective to decrease expression levels and/or activity of heparan sulfate in the skin of the subject is administered topically to the skin.

In aspects, a method of identifying a modulator of autophagy is provided, the method comprising contacting NDST, a substrate for NDST, and a test substance under reaction conditions that promote specific interaction between NDST and the substrate for NDST, and detecting a change in specific interaction between the NDST and the substrate for NDST. In aspects, the NDST substrate is N-acetylglucosamine (GlcNAc). In aspects, detecting a change in specific interaction between the NDST and the substrate for NDST comprises detecting formation of N-sulfo glucosamine (GlcNS) residues. In aspects, detecting a change in specific interaction between the NDST and the substrate for NDST comprises detecting heparan sulfate.

Aspects of the present invention relate to screening and assay methods, and substances identified thereby, for example, assays for compounds or substances that inhibit the activity of an NDST polypeptide on a substrate. In aspects, the substrate may be N-acetylglucosamine (GlcNAc) or GlcNAc residues.

Controls are well-known in the art and one of skill in the art would readily recognize an appropriate control and be able to determine an appropriate control for a method of the present invention with no more than routine experimentation.

According to aspects of a method for identifying a compound that modulates activity of an NDST polypeptide according to aspects of the present invention, which includes contacting a cell expressing an NDST polypeptide with a test compound and determining the effect of the test compound on activity of the NDST polypeptide, an appropriate control is determining the activity of the NDST polypeptide when a cell expressing the NDST polypeptide is not contacted with the test compound under the same or similar conditions.

An appropriate control may be a reference level of a variable such as activity of an NDST polypeptide, level of stability of the NDST polypeptide, level of secretion of a physiological target of the NDST polypeptide, and/or level of NDST polypeptide activity relative to an appropriate control, previously determined and stored in a print or electronic medium for recall and comparison to a determined effect of a test compound on activity of an NDST polypeptide according to aspects of a method for identifying a compound that modulates activity of an NDST polypeptide of the present disclosure.

An assay method for identifying a modulator of an NDST polypeptide may include bringing into contact an NDST polypeptide as described herein and a test compound, determining binding of the test compound to the NDST polypeptide, and determining the enzymatic activity of the NDST polypeptide in the presence and absence of a test compound that binds the NDST polypeptide. Enzymatic activity may be determined by determining the deacetylation and/or sulfo group transfer of a substrate as described below. The NDST polypeptide may be isolated or comprised in a liposome or cell.

As used herein with reference to NDST, the term "isolated" refers to NDST which is substantially free of other cellular material, such as other proteins or peptides, culture medium or culture medium components, where the NDST is produced by recombinant techniques, or substantially free of chemical precursors or other chemicals when NDST is chemically synthesized. The term "substantially free" refers to preparations including less than 25% (by dry weight) of non-NDST protein, less than 20% (by dry weight) of non-NDST protein, less than 15% (by dry weight) of non-NDST protein, less than 10% (by dry weight) of non-NDST protein, less than 5% (by dry weight) of non-NDST protein, less than 1% (by dry weight) of non-NDST protein, or less than 0.5% (by dry weight) of non-NDST protein. Further, the term "isolated" refers to NDST compositions which include at least 75% (by dry weight) of NDST, at least 85% (by dry weight) of NDST, at least 90% (by dry weight) of NDST, at least 95% (by dry weight) of NDST, at least 96% (by dry weight) of NDST, at least 97% (by dry weight) of NDST, at least 98% (by dry weight) of NDST, at least 99% (by dry weight) of NDST, or greater than 99% (by dry weight) of NDST.

A method of screening for and/or obtaining a substance/compound which modulates activity of an NDST polypeptide may include contacting one or more test substances or compounds with the NDST polypeptide in a suitable reaction medium, determining the activity of the treated polypeptide, and comparing that activity with the activity of the polypeptide in comparable reaction medium untreated with the test substance or substances. The NDST polypeptide may be in the reaction medium in an isolated form or may be present in a liposome or cell.

A difference in activity between the treated and untreated NDST polypeptides is indicative of a modulating effect of the relevant test substance or substances, for example, an inhibiting or enhancing effect.

Activity of an NDST polypeptide may be determined by determining the production of N-sulfo glucosamine (GlcNS). The NDST polypeptide may, for example, act on a substrate to generate a soluble GlcNS product which is detected.

According to another aspect of the present invention there is provided an assay method for identifying and/or obtaining a modulator of an NDST polypeptide, which method comprises: (a) bringing into contact an NDST polypeptide and a test compound in the presence of a substrate; and (b) determining deacetylation and/or sulfo group transfer of the substrate.

NDST is a bifunctional enzyme that converts GlcNAc residues to N-sulfo glucosamine (GlcNS) residues. The N-deacetylase domain removes the acetyl group from GlcNAc to form N-unsubstituted glucosamine (GlcNH2), whereas the N-sulfotransferase domain transfers a sulfo group to the GlcNH2 residues to form GlcNS. Thus, enzymatic activity of NDST refers to deacetylation, sulfo group transfer, and both deacetylation and sulfo group transfer.

Enzymatic activity on the substrate may be determined in the presence and absence of test compound. A difference in enzymatic activity in the presence of the test compound relative to the absence of test compound may be indicative of the test compound being a modulator of NDST enzymatic activity.

Any substrate that is deacetylated and/or undergoes sulfo group transfer by an NDST polypeptide may be used in an assay method as described herein. Such substrates are readily identified using standard techniques. In embodiments, the polypeptide substrate may be GlcNAc or a functional fragment thereof.

A suitable substrate may comprise a detectable label such as green fluorescent protein (GFP), luciferase or alkaline phosphatase. This allows convenient detection of the soluble enzymatic reaction product and is particularly useful in automated assays.

Preferably, suitable NDST substrates have greater than 50% homology, greater than 60% homology, greater than 70% homology, greater than 80% homology greater than 90% homology or greater than 95% homology to a vertebrate NDST substrate.

Assay methods or other methods for obtaining or identifying modulators of NDST activity according to the present invention may be in vivo cell-based assays, or in vitro non-cell-based assays (i.e. in silico).

In in vitro assays, the NDST polypeptide may be isolated or contained in a liposome. Liposome based assays may be carried out using methods well-known in the art.

Suitable cell types for in vitro assays include mammalian cells such as mouse embryonic fibroblasts, keratinocytes, HEK293, CHO, HeLa and COS cells.

It is not necessary to use the entire full length proteins for in vitro or in vivo assays of the invention. Polypeptide fragments which retain the activity of the full length protein may be generated and used in any suitable way known to those of skill in the art. Suitable ways of generating fragments include, but are not limited to, recombinant expression of a fragment from encoding DNA. Such fragments may be generated by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments (e.g. up to about 20 or 30 amino acids) may also be generated using peptide synthesis methods which are well known in the art.

The precise format of the assay of the invention may be varied by those of skill in the art using routine skill and knowledge. For example, interaction between the polypeptides may be studied in vitro by labeling one with a detectable label and bringing it into contact with the other which has been immobilized on a solid support. Suitable detectable labels include 35S-methionine which may be incorporated into recombinantly produced peptides and polypeptides. Recombinantly produced peptides and polypeptides may also be expressed as a fusion protein containing an epitope that can be labeled with an antibody.

Fusion proteins may be generated that incorporate six histidine residues at either the N-terminus or C-terminus of the recombinant protein. Such a histidine tag may be used for purification of the protein by using commercially available columns which contain a metal ion, either nickel or cobalt. These tags also serve for detecting the protein using, commercially available monoclonal antibodies directed against the six histidine residues.

Assays according to the present invention may take the form of in vitro assays. In vitro assays may be performed in a cell line such as a yeast strain, insect cell line or mammalian cell line in which the relevant polypeptides or peptides are expressed from one or more vectors introduced into the cell.

In assay and other methods according to such embodiments, an NDST polypeptide may be contacted with the test compound in the presence of a substrate, such as GlcNAc. In such methods, the NDST polypeptide and substrate may be present in a cell. This may be achieved, for example, by expressing the polypeptides from one or more expression vectors which have been introduced into the cell by transformation.

An assay method for identifying and/or obtaining a modulator of NDST enzymatic activity may therefore include: (a) bringing into contact an NDST polypeptide and a test compound in the presence of GlcNAc; and (b) determining one or more of deacetylation, sulfo group transfer, and formation of GlcNS.

Enzymatic activity may be determined in the presence and absence of a test compound. A difference in enzymatic activity in the presence, relative to the absence of a test compound is indicative of the compound being a modulator i.e. an enhancer or inhibitor of NDST activity.

A nucleic acid encoding an NDST polypeptide and/or polypeptide substrate as described above may be provided as part of a replicable vector, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as HEK, COS or CHO cells or in prokaryotic cells such as E. coli. This is discussed further below.

Combinatorial library technology provides an efficient way of testing a potentially vast number of different substances for ability to modulate activity of a polypeptide. Prior to or as well as being screened for modulation of activity, test substances may be screened for ability to interact with the polypeptide e.g. in a yeast two-hybrid system (which requires that both the polypeptide and the test substance can be expressed in yeast from encoding nucleic acid). This may be used as a coarse screen prior to testing a substance for actual ability to modulate activity of the polypeptide.

The amount of test substance or compound which may be added to an assay of the invention will normally be determined by trial and error depending upon the type of compound used. Typically, from about 0.01 to 100 nM concentrations of putative inhibitor or activator compound may be used, for example from 0.1 to 10 nM. When cell-based assays are employed, the test substance or compound is desirably membrane permeable in order to access the NDST polypeptide.

Test compounds may be natural or synthetic chemical compounds used in drug screening programs. Extracts of plants which contain several characterized or uncharacterized components may also be used. A further class of putative inhibitor or activator compounds can be derived from the NDST polypeptide and/or a ligand which binds. Membrane permeable peptide fragments of from 5 to 40 amino acids, for example, from 6 to 10 amino acids may be tested for their ability to disrupt such interaction or activity.

In one embodiment, compounds for modulating (e.g., increasing or decreasing) the activity of an NDST polypeptide may be small molecule compounds. In another embodiment, the compound is cell-permeable. In embodiments, the compound is an antisense molecule, an aptamer, siRNA shRNA, miRNA, a DNAzyme, or a ribozyme. In embodiments, the compound is an antibody. In embodiments, the compound is a decoy agent.

Other test compounds may be based on modeling the 3-dimensional structure of a polypeptide or peptide fragment and using rational drug design to provide potential inhibitor compounds with particular molecular shape, size and charge characteristics.

Following identification of a substance which modulates or affects polypeptide activity, the substance may be investigated further. Furthermore, it may be manufactured and/or used in preparation, i.e. manufacture or formulation, of a composition such as a medicament, pharmaceutical composition or drug. Such compositions may be administered to individuals suffering from diseases associated with modulation of autophagy.

Another aspect of the present invention provides the use of an NDST polypeptide as described herein in a method for obtaining or identifying a modulator, for example an inhibitor, of NDST enzymatic activity. Also provided are methods and uses of an NDST polypeptide in the deacetylation, sulfo group transfer, and formation of GlcNS or GlcNS residues.

Modulators, in particular inhibitors of NDST activity are useful in the treatment of neurodegenerative diseases, for example, Alzheimer's Disease, Parkinson's disease, Huntington's disease, amyotrophic lateral sclerosis, and a prion encephalopathy.

In aspects, a method of identifying a modulator of autophagy is provided, the method comprising contacting an N-deacetylase N-sulfotransferase (NDST) polypeptide, a substrate for NDST, and a test substance under reaction conditions that promote specific interaction between the NDST polypeptide and the substrate for NDST, and detecting a change in specific interaction between the NDST polypeptide and the substrate for NDST. In aspects, the NDST substrate is N-acetylglucosamine (GlcNAc).

In certain aspects, detecting a change in specific interaction between the NDST polypeptide and the substrate for NDST comprises detecting formation of N-sulfo glucosamine (GlcNS). In certain aspects, detecting a change in specific interaction between the NDST polypeptide and the substrate for NDST comprises detecting heparan sulfate.

In aspects, the NDST polypeptide is an isolated NDST polypeptide.

In aspects, the method further comprises comparing the specific interaction between the NDST polypeptide treated with the test substance and the NDST substrate with a control. In embodiments, the control comprises specific interaction between an NDST polypeptide not treated with the test substance and the NDST substrate.

```
GenBank: AAH12888.1
Human NDST1 is shown herein as
                                                  SEQ NO: 1
MPALACLRRLCRHVSPQAVLFLLQVVCQFSVFISAYYLYGWKRGLEP

SADAPEPDCGDPPPVAPSRLLPLKPVQAATPSRTDPLVLVFVESLYS

QLGQEVVAILESSRFKYRTEIAPGKGDMPTLTDKGRGRFALIIYENI

LKYVNLDAWNRELLDKYCVAYGVGIIGFFKANENSLLSAQLKGFPLF

LHSNLGLKDCSINPKSPLLYVTRPSEVEKGVLPGEDWTVFQSNHSTY

EPVLLAKTRSSESIPHLGADAGLHAALHATVVQDLGLHDGIQRVLFG

NNLNFWLHKLVFVDAVAFLTGKRLSLPLDRYILVDIDDIFVGKEGTR
```

-continued

```
MKVEDVKALFDTQNELRAHIPNFTFNLGYSGKFFQTGTNAEDAGDDL

LLSYVKEFWWFPHMWSHMQPHLFHNQSVLAEQMALNKKFAVEHGIPT

DMGYAVAPHHSGVYPVHVQLYEAWKQVWSIRVTSTEEYPHLKPARYR

RGFIHNGIMVLPRQTCGLFTHTIFYNEYPGGSSELDKIINGGELFLT

VLLNPVSAPQPMAAGEKGLLHSLSAADTGFLEPGKGGEA.
```

Particular aspects of the present invention relate to NDST having an amino acid sequence that has at least about 85%, 90%, 91%, 92%, 93%, 94%, 95%, 96%, 97%, 98%, 99%, or greater, sequence identity with the amino acid sequence set forth in SEQ ID NO:1, such as human NDST2, human NDST3, human NDST4, and non-human orthologs thereof.

To determine the percent identity of two amino acid sequences or two nucleotide sequences, the sequences are aligned for optimal comparison purposes (e.g., gaps can be introduced in a first amino acid or nucleotide sequence for optimal alignment with a second amino acid or nucleotide sequence using the default parameters of an alignment software program). The amino acids or nucleotides at corresponding amino acid positions or nucleotide positions are then compared. When a position in the first sequence is occupied by the same amino acid or nucleotide as the corresponding position in the second sequence, then the sequences are identical at that position. The percent identity between the two sequences is a function of the number of identical positions shared by the sequences (i.e., % identity=number of identical aligned positions/total number of aligned positions 100%). In some embodiments, the two sequences have the same length.

The determination of percent identity between two sequences can be accomplished using a mathematical algorithm. A non-limiting, example of a mathematical algorithm utilized for the comparison of two sequences is the algorithm of Karlin and Altschul, 1990, PNAS USA 87:2264-68, e.g., as modified as in Karlin and Altschul, 1993, PNAS USA 90:5873-77. Such an algorithm is incorporated in the NBLAST and XBLAST programs of Altschul et al, 1990, J. Mol, Biol. 215:403. BLAST protein searches can be performed with the XBLAST program parameter set, e.g., to score 50, wordlength=3, to obtain amino acid sequences homologous to a protein molecule of the present invention. To obtain gapped alignments for comparison purposes, Gapped BLAST can be utilized as described in Altschul et al, 1997, Nucleic Acids Res. 25:3389-02. Alternatively, PSI BLAST can be used to perform an iterated search that detects distant relationships between molecules (id.). When utilizing BLAST, Gapped BLAST, and PSI Blast, the default parameters of the respective programs (e.g., of XBLAST and NBLAST) are used (see, e.g., the NCBI website). Another preferred, non-limiting example of a mathematical algorithm utilized to compare sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used. The Clustal suite of software programs provides an additional method for aligning sequences to determine percent sequence identity.

Conservative amino acid substitutions can be made in the NDST protein to produce NDST variants. Conservative amino acid substitutions are art recognized substitutions of one amino acid for another amino acid having similar characteristics. For example, each amino acid can be described as having one or more of the following characteristics: electropositive, electronegative, aliphatic, aromatic, polar, hydrophobic, and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine, and valine; aromatic amino acids include phenylalanine, tyrosine, and tryptophan; polar amino acids include aspartate, glutamate, histidine, lysine, asparagine, glutamine, arginine, serine, threonine, and tyrosine; and hydrophobic amino acids include alanine, cysteine, phenylalanine, glycine, isoleucine, leucine, methionine, proline, valine, and tryptophan; and conservative substitutions include substitutions among amino acids within each group. Amino acids can also be described in terms of sterics or relative size, e.g., alanine, cysteine, aspartate, glycine, asparagine, proline, threonine, serine, and valine are all typically considered to be small.

Mutations can be introduced using standard molecular biology techniques such as site-directed mutagenesis and PCR-mediated mutagenesis. One of skill in the art will recognize that one or more amino acid mutations can be introduced without altering the functional properties of NDST.

Embodiments of inventive compositions and methods are illustrated in the following examples. These examples are provided for illustrative purposes and are not considered limitations on the scope of inventive compositions and methods.

EXAMPLES

The following detailed methodology and materials are set forth to support and illustrate particular aspects and embodiments of the invention, and should not be construed as limiting the scope thereof.

Example 1. Materials and Methods

Lifespan and Log-Rank Analysis

A typical experiment began with over 100 adult flies. Flies were examined for longevity on standard media at 25° C., 25-30 animals per vial, and transferred to new media every 48 hours. Mortality was scored every 48 hours. Significant deviation in survival curves was calculated first on the pooled genotypes by logrank test using the Mantel-Haenszei method, followed by pair-wise comparison between each experimental genotype and the control using the Gehan-Breslow-Wilcoxon test. No individuals were censored during the survival assay, and survival curves of the experimental genotypes do not cross that of the control.

Survival curves can be compared using the log-rank test to ascertain whether or not there are differences in the survival experiences of two genotypes. In the absence of censoring, the log-rank test assumes that survival probability is the same for individuals recruited at different time points and that mortality events happened at the times specified. Log-rank uses a chi-square analysis of the number of deaths and number of expected deaths at each time point over the course of the study to calculate differences between two groups. The number of expected deaths for genotype A at timepoint x ($E_{Ax}$) is calculated by taking the combined number of deaths of all genotypes in the comparison ($d_x$) multiplied by the ratio of individuals of genotype A remaining at time x ($n_{Ax}$) to the combined number of individuals remaining in both genotypes at time x ($n_x$). This can be summarized by $E_{Ax}=d_x(n_{Ax}/n_x)$. This calculation must be done at all time points for all genotypes being compared. The total numbers of expected deaths (E) and the total number of observed deaths (O) for each genotype can then be calculated. The test is the statistic sum of $(O-E)^2/E$ for each genotype resulting in a chi square value with one degree of freedom and ultimately a p-value representing significant difference between two survival curves, see Bewick, V., et al., 2004, Crit. Care 8:389-394 for additional details of the statistical method.

Oxidant Exposure

Hydrogen peroxide toxicity was performed to observe ROS sensitivity. One-week old flies were placed in vials at 25° C., 20 per vial, and with food media made of 1% sucrose, 1% dry yeast extract, 1.2% agar (w/v), and 1.5% hydrogen peroxide as described in detail in Cumming, R. C., et al., 2008, Methods Enzymol., 451:639-651. In addition to the ROS exposed set, a control set using the same conditions in the absence of hydrogen peroxide was done for each genotype. Mortality was scored every 12 hours and the media was replaced every 24 hours.

Flight Assay

Flight assays were conducted according to protocols described in detail in Kawasaki, F., et al., 2016, Dis. Model Mech. 9; 953-964. Briefly, adults flies are introduced into the top of a large diameter cylinder coated with oil. Flies stick to the wall of the cylinder when they land and the height of their landing provides a measure of their capacity to maintain flight; flightless animals fall to a pool of oil at the bottom of the cylinder.

Immunohistochemistry and Confocal Analysis

Whole-mount immunostaining of adult flight muscles was carried out to visualize both ubiquitin levels and the organization of actin filaments according to procedures described in Hunt, L. C., et al., 2013, Nat. Protoc., 8:2496-2501. Images were acquired at room temperature using an Olympus Fluoview FV1000 laser-scanning confocal microscope (Olympus America, Waltham, Mass., USA), FV10-ASW 2.1 software (Olympus, Waltham, Mass., USA) was used to capture images. When more than one fluorophore was detected, sequential line scanning was performed to avoid spectral bleed through artifacts. Images of samples with different genotypes within a single experiment were captured, processed, and analyzed using the same setting. Images were presented as Z-stacks of maximum intensity projections using Imaris 7.3 software (Bitplane Inc.). All adjustments to contrast and brightness made to ease interpretation of confocal images were applied identically to all genotypes within each experiment.

Image Analysis of Ubiquitin-Positive Intracellular Punctae in Flight Muscle

ImageJ was used to identify and measure the number of anti-ubiquitin antibody-positive punctae in the adult flight muscles of sfl park$^{\Delta 21}$/mef2-Gal4 park$^1$ and UAS-Atg5$^{RNAi}$/+; sfl park$^{\Delta 21}$/mef2-Gal4 park$^1$ animals. Animals were reared at 25° C. for the experiments illustrated in FIG. 9. The presence of the UAS-Atg5$^{RNAi}$ adversely affected survival of park$^{\Delta 21}$/mef2-Gal4 park$^1$ (less than 10% of expected, n=733). For every image, the brightness of the color threshold was set to a minimum of 70, to identify the punctae over background. The "Measure" function was used to determine the area and the "Particles" function was used to count the number of particles, with the circularity of the particles set to the restraints of 0.80-1.00. The "Exclude on Edges" function was enabled to remove extraneous staining at the edges of the preparation, and the number of punctae per unit area was determined. Differences between punctae/area for the genotypes was assessed using a two-tailed t-test. A replicate experiment conducted at a lower temperature (23° C.), where Gal4 activity is less, and hence RNAi of Atg5 lower, allowed for improved survival of sfl park$^{\Delta 21}$/mef2-Gal4 park$^1$ animals. The presence of UAS-Atg5$^{RNAi}$ increased the number of ubiquitin-positive punctae in sfl park$^{\Delta 21}$/mef2-Gal4 pare animals reared at this temperature but reducing the brightness thresholds to 40 was required to detect the intracellular punctae. The rectangle tool was used to select a 60-pixel by 60-pixel sampling area for each preparation and the circularity set to 0.7-1.0, UAS-Atg5$^{RNAi}$/+; mef2-Gal4 park$^1$/+ animals served as controls to determine the interaction between Atg5$^{RNAi}$ and park function. Elevated levels of punctae required two mutant alleles of park (sfl park$^{\Delta 21}$/mef2-Gal4 park$^1$).

Eye Morphometry and Presenilin Overexpression Experiments

UAS-Psn is a 541 amino acid wildtype Presenilin coding sequence. This construct was overexpressed pan-neuronally under the control of elav(C15)-Gal4>UAS-DcrII. This Gal4-expressing line also incorporates UAS-based overexpression of DcrII, which is needed to elicit effective RNAi in neurons. The UAS-Psn construct was expressed on its own and in combination with several RNAi lines. Eyes were imaged using an Olympus BX53 compound microscope and Olympus cellSens Dimension software (Olympus Optical, Waltham, Mass.) to obtain optical sections at a 9 μm step. Optical sections for each animal were assembled into a single composite image using Zerene Stacker (Zerene Systems LLC, Richland, Wash.). Eye area was measured in ImageJ and ommatidial organization was assessed using the Flynotyper ImageJ plugin. Statistical analysis, of the results were performed using GraphPad Prism software (version 8.1.2). First, D'Agostino and Pearson normality testing was performed for all genotypes, separated by gender. Kruskal Wallis non-parametric testing was then used since all samples were not normally distributed to determine if there were any significant differences between the groups. This pooled testing was followed by Uncorrected Dunn's Test for pairwise comparisons, providing the p-values provided for the scatter plots in FIGS. 5E and 5F.

Fly Rearing and Strains

Fly strains were raised on standard cornmeal/sucrose/agar media at 25° C. Oregon-R, UAS-w RNAi (30033), and VDRC60100 strains served as controls; stock numbers are listed in parentheses. Unless otherwise specified, when UAS-sfl RNAi is shown, UAS-sfl RNAi HMS00543 (34601) strain was used. RNAi strains and a control strain with the same genetic background were obtained from the Vienna *Drosophila* RNAi Center (VDRC); UAS-Atg8a RNAi (43097), UAS-sfl RNAi (5070), UAS-ttv RNAi (4871), UAS-w RNAi (30033) and empty vector control (60100). UAS-Atg5 RNAi is Bloomington Stock number 27551.

Figures 11A, 11B, 11C:
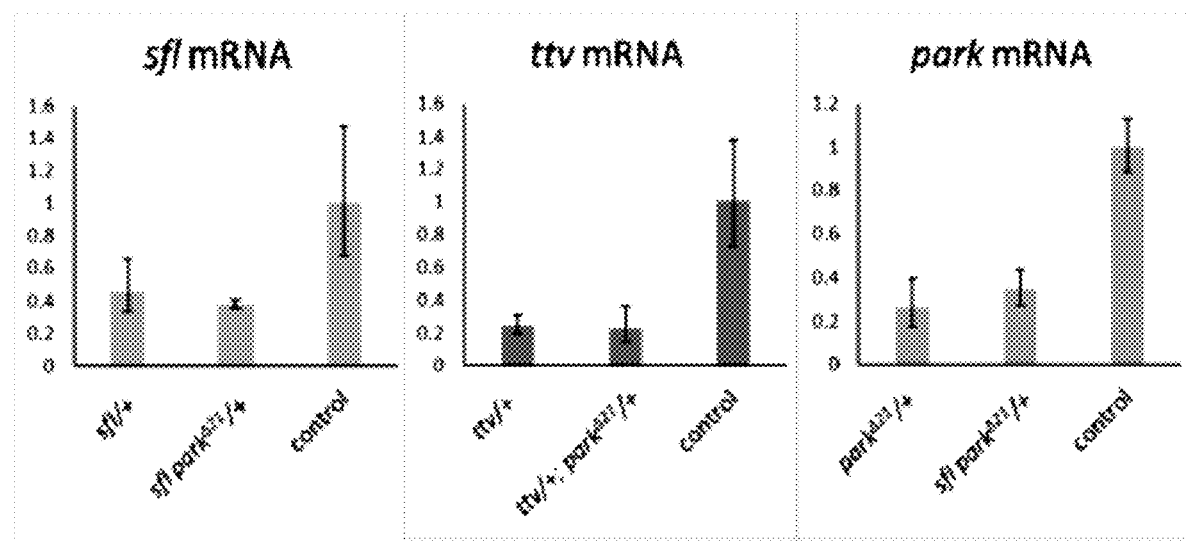
FIG. 11A is a graph showing results of quantitative PCR analysis of sfl mRNA and showing the levels of sfl mRNA in animals bearing a sfl03844 null allele recombined onto a parkΔ21 bearing chromosome.
FIG. 11B is a graph showing results of quantitative PCR analysis of ttv mRNA and showing the ttv mRNA levels in animals used for the genetic interaction experiments described.
FIG. 11C is a graph showing results of quantitative PCR analysis of park mRNA and showing the park mRNA levels in animals used for the genetic interaction experiments described.

UAS-mcherry-Atg8a (37750), elav$^{C155}$-Gal4>UAS-DcrII (25750), UAS-Atg8a (10107), UAS-Psn$^{541}$ (8309) and the *Drosophila* Transgenie RNAi Project (TRIP) lines UAS-sfl RNAi GLC01656 (50538), UAS-sfl RNAi HMS00543 (34601), and UAS-mCherry RNAi (35785) were obtained from the Bloomington *Drosophila* Stock Center (BDSC). The sfl$^{03844}$ and ttv$^{00681}$ P-element insertion alleles were generated by the Berkeley *Drosophila* gene disruption project and have been previously described. The sfl$^{9B4}$ ethyl methanesulfonate-induced point mutation was generated and described by Norbert Perrimon. parkin alleles (park$^1$, park$^{A21}$) were obtained from the Bloomington Stock Center. sfl park$^{A21}$ recombinant chromosomes were generated and the presence of sfl and parkin alleles determined by back crossing to lethal sfl and parkin alleles, as well as by PCR analysis of recombinant animals and QPCR to measure mRNA levels (see FIG. 11). Four recombinants of the two different sfl alleles were generated and evaluated, botv$^{423}$ is a point mutation and loss-of-function allele, see Takei, Y., et al., 2003, Development, 131:73-82. UAS-mitoGFP (P-element insertion on the second chromosome, Bloomington stork number 8442) was used to selectively tag mitochondria and muscle specific expression was achieved using mef2-Gal4 (y$^1$w$^6$; P{GAL4-Mef2.R}3 on the third chromosome, Bloomington stock number 27390).

mCherry Conversion Assay

Pan-neuronal expression was, achieved using elavC155-Gal4 with UAS-DcrII to enhance RNAi efficacy and the UAS-mCherry-Atg8a reporter construct, UAS-w RNAi was used as a control. Overexpression of wildtype Atg8a was used as a positive control for enhanced autophagy. Density of the parental mCherry-Atg8a band was divided by density of the free mCherry band to determine the ratio of fluorophore conversion. For the mCherry conversion assay, 30-60 adult heads were homogenized by ceramic bead agitation using the using a Bead Ruptor 24 (Omni International, Kennesaw, Ga., 73 USA) in 100 µl of SDS extraction buffer (2% SDS, 50 mM Tris pH7.4, 1× protease inhibitor cocktail Complete [Roche, 10184600]). Samples were spun down at 10,000 rpm for 10 minutes and the supernatant was removed to a clean tube.

Insoluble Ubiquitin Protein Assay

A two-step protein extraction was used for Insoluble Ubiquitin Protein analysis, modified from the method described by Cumming, Simonsen and Finley, 2008. Typically, 30-60 adult heads were homogenized by ceramic bead agitation using the Bead Ruptor 24 in 150 ul of Tritonx-100 extraction buffer (1% Triton-X100, 1×PBS, 1× protease inhibitor cocktail Complete [Roche, 10184600]). Samples were spun down at 10,000 RPM for 10 minutes at 4° C. The supernatant was drawn off and saved as the soluble protein fraction. The pellets were washed with 100 ul of TritonX-100 before being resuspended in 100 ul of 2% SDS extraction buffer. Supernatant from this extraction was saved and is referred to as the TritonX insoluble fraction. Protein sample concentration was determined by RCA Protein Assay (Pierce, 23227).

Western Blotting

IUP assessment utilized 9% acrylamide gels, while the analysis of mCherry-Atg8a utilized 6% acrylamide gels. PAGE was performed using the BioRad mini-PROTEAN electrophoretic and transfer system (BioRad, Hercules Calif.) with 1 mm plates. Protein samples were prepared for loading and membranes were processed as described above. Primary antibody incubation was performed overnight at 4° C. using 1:2000 mouse anti-Mono- and Polyubiquitinylated Conjugates (FK2) (Eras, BML-PW8810-0100) or 1:2000 rabbit anti-mCherry (abeam, ab183628), and 1:3000 mouse anti-tubulin (Developmental Studies Hybridoma Bank, 12G10). Secondary antibody incubation (1:3000 HRP conjugated goat anti-mouse or rabbit, Invitrogen, 31430 and 7431460) was performed for 45 minutes at room temperature. ECL detection and band densitometry were performed as described above. For loading analysis, a combination of Ponceau staining and stripping and reprobing with anti-alpha tubulin was used. Membranes were stripped for re-probing in mild stripping buffer (0.1% SDS, 1.0% Tween20, 0.2M glycine, pH 2.2). All blotting experiments were performed using three biological replicates for each genotype under each condition. Lanes with the most numerically similar sample loading, as determined by densitometry, were chosen from within the biological triplicates for display.

Quantitative Reverse Transcription PCR

QPCR assays of sfl, ttv and parkin were carried out to evaluate the levels of these transcripts in animals heterozygous for sfl or ttv alleles and either heterozygous or homozygous for park alleles. Transcript levels were also measured in larvae bearing UAS-sfl$^{RNAi}$ or UAS-ttv$^{RNAi}$ expressed under the control da-Gal4.

RNA was isolated from 20 flies per sample with a Machery-Nagel DNA, RNA and Protein Purification Kit. RNA was diluted to 200 ng/ul then used in a High Capacity cDNA Reverse Transcription Kit (Applied Biosystems). This was put through an Eppendorf Mastercycler Pro PCR machine to create cDNA. Real time PCR was performed in a StepOne machine, using TaqMan assays for *Drosophila* gene targets park, sfl, ttv, and arginine kinase (Thermo Fisher Scientific).

Data was analyzed using Thermo Fisher Connect software to determine the relative quantifications. Three biological replicates with two technical replicates were used for each genotype. Target gene data was normalized to arginine kinase using tire ΔΔCt method.

Statistical Analysis

Statistical analyses of quantitative data Were performed using either Minitab Release 16 (Minitab) or GraphPad Prism 81.2 (GraphPad Software). Data were represented as the mean±95% confidence interval unless otherwise indicated. Data distributions were tested using D'Agostino & Pearson normality test. Comparisons between more than two groups were performed using ANOVA or Kruskal-Wallis for nonparametric and or heteroscedastic data, followed by individual pairwise comparisons using Dunn's test for nonparametric data or a Most for normally distributed data.

Example 2. RNAi of Genes Required for Heparan Sulfate Biosynthesis Increase Autophagy-Dependent Cleavage of Atg8a in the Brain Earlier work demonstrated that reducing heparan sulfate biosynthesis increased autophagy in muscle and fat body, the latter being the principle metabolic sensing and energy storage tissue in *Drosophila*. Given the critical role autophagy plays in neurodegenerative processes, the investigators sought to determine directly if heparan sulfate biosynthesis affects autophagy in the brain. Autophagy-mediated proteolysis produces cleavage of key components, including Atg8a, a protein involved in autophagosome formation. Monitoring Atg8a cleavage is therefore one measure of autophagy. To evaluate Atg8a proteolytic processing, an mCherry-Atg8a fusion protein was expressed in the brain using a UAS-mCherry-Atg8a construct and a neuron-specific Gal4 transcriptional activator. The resistance of the mCherry domain of the fusion protein to depradation allows the visualization of a relatively stable proteolytic product detected with an anti-mCherry antibody. The ratio of the parental protein, mCherry-Atg8a, to the mCherry proteolytic product provides a measure of autophagy-dependent activity (FIG. 1).

As previously reported, activation of autophagy by transgene expression of Atg8a produced greater conversion of the mCherry-Atg8a fusion protein to the smaller mCherry-containing fragment. Knockdown of either of two genes required for heparan sulfate biosynthesis, sulfateless (sfl) or tout velu (ttv) increased Atg8a proteolysis. sfl, encodes N-deacetylase N-sulfotransferase, an enzyme affecting sulfation of the heparan sulfate polymer. ttv encodes a homolog of Exostosin 1 (Ext1), a glycosyl transferase critical for heparan sulfate chain elongation. RNAi of either sfl or ttv produced a greater degree of proteolytic cleavage of mCherry-Atg8a, indicative of a net increase in autophagy in the CNS (FIG. 1).

Reducing heparan sulfate biosynthesis showed the hallmarks of increased autophagy, including elevated cleavage of Atg8a. These findings demonstrate the capacity of heparan sulfate levels to affect authophagy in the brain and indicate that heparan sulfate modified protein-mediated regulation of autophagy is widely represented in different tissues and developmental states.

Figure 2A:
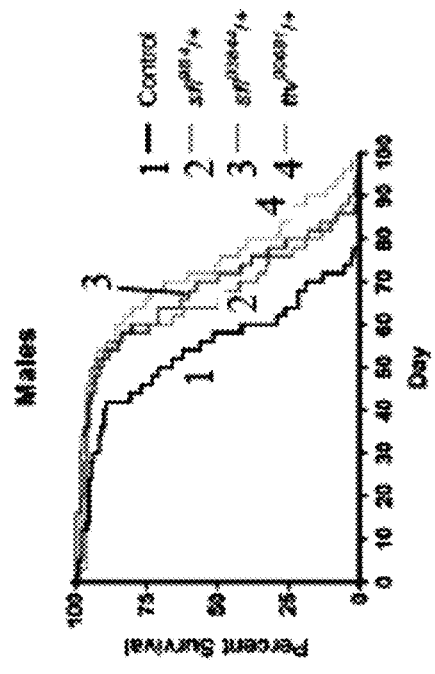
FIG. 2A is a graph showing that reducing function of key HS biosynthetic genes increases lifespan in females. Animals heterozygous for alleles of either sfl, or ttv were examined for lifespan under normal culture conditions. Reductions in the functions of either of these HS biosynthetic genes significantly extended lifespan ($p<0.0001$ compared to control for each gender and genotype).
Figure 2B:
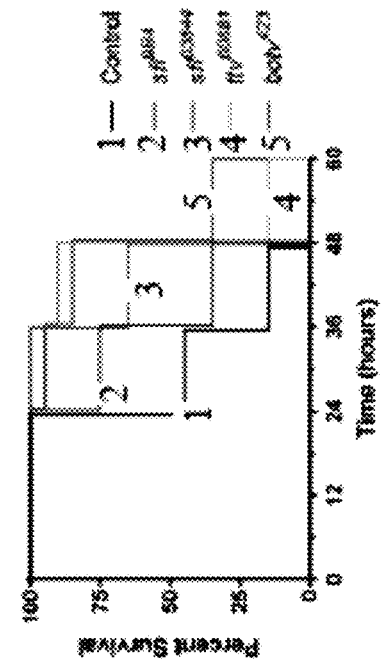
FIG. 2B is a graph showing that reducing function of key HS biosynthetic genes increases lifespan in males; Animals heterozygous for alleles of either sfl, or ttv were examined for lifespan under normal culture conditions. Reductions in the functions of either of these HS biosynthetic genes significantly extended lifespan ($p<0.0001$ compared to control for each gender and genotype).

Example 3. Reductions of Heparan Sulfate Biosynthetic Gene Function Increase Lifespan Increases in autophagy can extend lifespan, and longevity therefore provides a measure of autophagy function in the organism. Lifespan was evaluated in adult animals heterozygous for mutations in sfl or ttv, each affecting different components, of the heparan sulfate biosynthetic apparatus. Reducing the function of either of these two genes provided significant extension of lifespan compared to wild type control animals in both males and females (FIG. 2). Overall, ttv/+ appears to increase lifespan to a greater degree than sfl/+ animals. While the basis of these differences are not yet understood, heterozygosity for mutations in these genes does affect the levels and structure of the heparan sulfate polymer differently (see Table 1, below), perhaps accounting for the differential effects on lifespan. Together, these data provide evidence of the systemic impact of heparan sulfate modified proteins on the physiology of the organism consistent with an increase in autophagy levels.

In Table 1, each sample represents the average of samples containing 50 females and 50 adult males, where total heparan sulfate was purified and measured using a disaccharide profiling method described previously (Toyoda, et al. *Structural analysis of glycosaminoglycans in Drosophila and Caenorhabditis elegans and demonstration that toutvelu, a Drosophila gene related to EXT tumor suppressors, affects heparan sulfate in vivo, J. Biol. Chem.* 275(4): 2269-75 (2000b)).

TABLE 1

Analysis of heparan sulfate levels and structure in sfl and ttv heteroxygotes
Unsaturated disaccharide

|  | Total amount ng/mg dry tissue | NAc | NS | NAc6S | NS6S | 2SNS | 2SNS6S |
|---|---|---|---|---|---|---|---|
|  |  | % change compared to wild type | | | | | |
| OreR (wild type) | 12.8 | | | | | | |
| Slf$^{03844}$/+ | 10.1 | −2% | −18% | −8% | −12% | −19% | 6% |
| slf$^{9B4}$/+ | 10.1 | −8% | −21% | −7% | −7% | −21% | −4% |
| Ttv$^{00681}$/+ | 7.9 | −32% | −35% | −23% | −23% | −30% | −21% |

NAc = 2-acetamido-2-dexy-4-O-(4-deoxy-α-l-threo-hex-enepyranosyluronic acid)-d-glucose (ΔUA-GlcNAc); NS = 2-deoxy-2-sulfamido-4-O-(4-deoxy-α-l-threo-hex-enepyranosyluronic acid)-d-glucose (ΔUA-GlcNS); NAc6S = 2-acetamido-2-deoxy-4-O-(4-deoxy-α-l-threo-hex-enepyranosyluronic acid)-6-O-sulfo-d-glucose (ΔUA-GlcNAc6S); NS6S = 2-deoxy-2-sulfamido-4-O-(4-deoxy-2-O-sulfo-α -l-threo-hex-enepyranosyluronic acid)-6-O-sulfo-d-glucose (ΔUA-GlcNS6S); 2SNS = 2-deoxy-2-sulfamido-4-O-(4-deoxy- 2-O-sulfo-α-l-threo-hex-enepyranosyluronic acid)-d-glucose (ΔUA2S-GlcNS); 2SNS6S = 2-deoxy-2-sulfamido-4-O-(4-deoxy-2-O-sulfo-α-l-threo-hex-enepyranosyluronic acid)-6-O-sulfo-d-glucose (ΔUA2S-GlcNS6S).

Given the effect of heterozygosity for genes required for heparan sulfate biosynthesis on lifespan, it was of interest to determine the structure and levels of the heparan sulfate polymer in adult animals bearing these genotypes. Disaccharide profiling of heparan sulfate derived from ttv/+ and sfl/+ animals compared to wild type controls was conducted using a method that provides both levels and composition of six disaccharides that comprise the polymer. These analyses demonstrated that reducing the gene function by approximately 50%, with heterozygosity for alleles of either sfl or ttv, had a detectable and significant effect on both the quantity and sulfation state of the heparan sulfate polymer. In two different and independently isolated sfl alleles, heterozygosity lowered the levels of heparan sulfate-derived disaccharides by approximately 20% (Table 1) and also altered the sulfation pattern, reflected ins the levels of different mono, bi, and tri-sulfated disaccharides. Two disaccharides, the monosulfated NS(ΔUA-GlcNS), and the disulfated 2SNS (ΔUA2S-GlcNS), were affected the most, reduced by approximately 20% compared to wild type animals. Animals heterozygous for a ttv null allele, showed lower amounts of all disaccharides, to levels between 65-79% of wild type but without remarkable changes in the sulfation pattern. Previous analysis of third instar larvae heterozygous for ttv showed similar effects. These results are consistent with the established activities encoded by sfl and ttv.

Reducing the function of ttv or sfl increased lifespan significantly, providing evidence that compromising processes supported by heparan sulfate modified proteins was protective to a physiologically relevant degree and consistent with broadly elevated levels of autophagy.

Results further show that modest reductions in heparan sulfate biosynthesis are indeed not lethal, but actually increase lifespan and resistance to ROS stress. While not desiring to be bound by theory, it is believed that changing heparan sulfate structure to a modest degree that does not compromise some of the vital functions of heparan sulfate modified proteins allows the beneficial effects of removing inhibitory activities on cellular processes, such as increased autophagy, to become apparent. These pathways, both heparan sulfate biosynthesis and autophagy, are not "all or none" switches, but can have different effects depending on their level of function.

Measurable but modest changes in heparan sulfate levels and sulfation have a profound effect on the biology of the animal, indicating that pharmaceutical intervention that significantly increases autophagy does not require abrogation of heparan sulfate synthesis or modification. Similar reductions in heparan sulfate levels are observed in mice heterozygous for Ext1 or Ext2, two homologs of ttv, indicating that the effect of partial reductions in heparan sulfate biosynthetic function on heparan sulfate levels is conserved across diverse species.

Example 4. Reducing Heparan Sulfate Biosynthetic Capacity Increases Resistance to ROS Stress Reactive oxygen species (ROS) can contribute to cell damage and molecular systems designed to remove these molecules provide important cell protective mechanisms. Increasing autophagy provides protection against exposure to ROS stress by elevating the capacity of cells to remove damaged macromolecules. First, a principal source of ROS, mitochondria, is removed by an autophagy-dependent mechanism, mitophagy. In particular, damaged mitochondria, that produce higher levels of ROS, are tagged for removal and lysosomal degradation mediated by autophagocytosis. Autophagy is also able to remove damaged proteins and protein aggregates that can result from ROS damage.

Figure 3A:
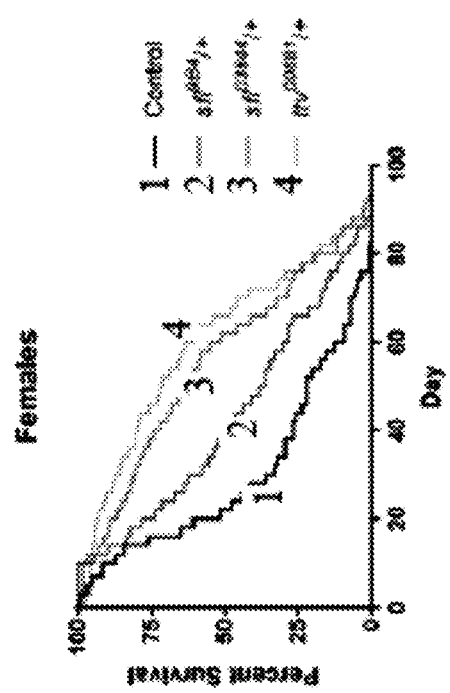
FIG. 3A is a graph showing that reduced function of key HS biosynthetic genes increases tolerance of oxidative stress in females; Adult flies were exposed to food containing 2% H2O2. Heterozygosity for each of these biosynthetic genes improved survival to this challenge; Females, compared to control: $p<0.0001$ all genotypes.
Figure 3B:
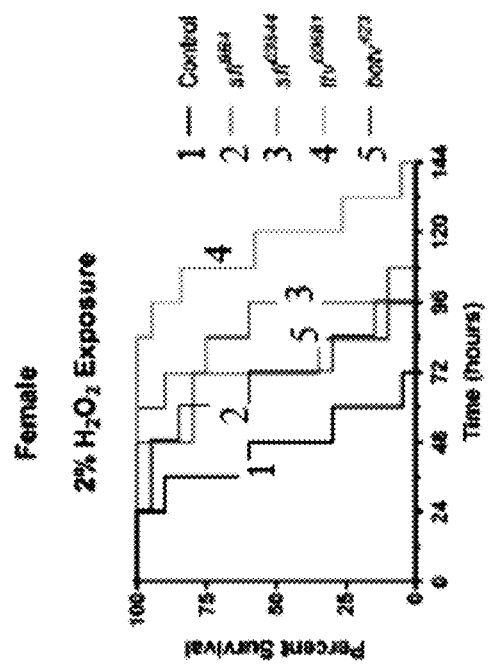
FIG. 3B is a graph showing that reduced function of key HS biosynthetic genes increases tolerance of oxidative stress in males; Adult flies were exposed to food containing 2% H2O2. Heterozygosity for each of these biosynthetic genes improved survival to this challenge; Males, compared to control: $p<0.05$ sfl9B4; $p<0.0001$ sfl03844, ttv00681, botv423.

Given the broad increases in autophagy measured in whole larvae, larval muscle and fat body, as well as adult brain upon reduction of heparan sulfate biosynthesis, the present investigators explored whether organism-wide decreases in heparan sulfate gene function could affect responses to oxidative stress. Measures of resistance to ROS exposure were therefore conducted for animals heterozygous for mutant alleles of sfl, ttv, and brother of ttv (botv) (FIG. 3). botv encodes the homolog to vertebrate EXT Like-3, an N-acetylglucosamine transferase-II required for heparan sulfate synthesis. To examine ROS sensitivity, adult flies were continuously exposed to $H_2O_2$ in food media and their survival monitored. Reductions in heparan sulfate biosynthetic gene function significantly increased survival to ROS exposure for all animals heterozygous for mutations in either of these three heparan sulfate biosynthetic enzyme-encoding genes. In female animals, wild type controls had a median survival duration of 48 hours, while $sfl^{9B4}/+$ or $sfl^{03844}/+$ survived for a median of 72 and 96 hours respectively. Heterozygosity for ttv further extended median survival to 120 hours, while botv/+ animals survived for a median of 72 h (FIG. 3A). Males were more sensitive to peroxide exposure than females, but heterozygosity for all of these alleles still significantly increased their tolerance (FIG. 3B). These findings indicate that compromising heparan sulfate gene function can have a significant impact on a whole-organism response to ROS.

Example 5. Knockdown of Heparan Sulfate Biosynthetic Enzyme Encoding Genes in the Brain Reduces Levels of Insoluble Ubiquitin-Modified Proteins Upon ROS Exposure Ubiquitin-modified proteins are subject to targeted autophagic degradation through binding to the autophagy receptor p62. Particularly in mature adults, levels of autophagy in a tissue are generally inversely proportional to the amount of ubiquitin present. We assessed the levels of insoluble ubiquitin-modified proteins isolated from the brains of adult animals with CNS-directed RNAi of sfl or ttv after a 24-hour exposure to control or $H_2O_2$-containing food. Adult heads were isolated, the proteins solubilized, and the Triton X-100 insoluble fraction obtained according to published protocols (Simonsen, et al., *Promoting basal levels of autophagy in the nervous system enhances longevity, and oxidant resistance in adult Drosophila, Autophagy* 4(2) 176-84 (2008)). This fraction was separated by SDS-PAGE and ubiquitin-modified proteins detected by western blotting. This procedure has been used to detect age- and autophagy-dependent changes in the clearance of ubiquitin-modified substrates in the CNS of adult *Drosophila*. The levels of ubiquitin were measured for the entire lane for each sample and the levels normalized by comparison to the signal detected with anti-tubulin antibody.

Figure 4:
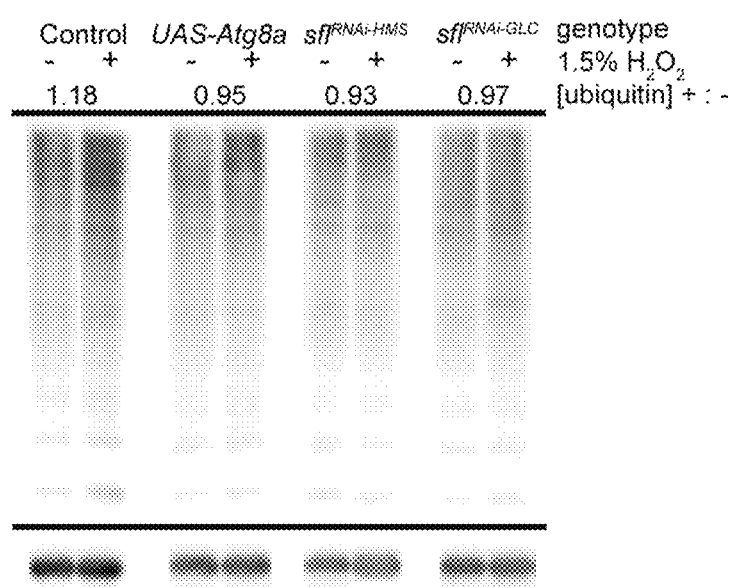
FIG. 4 is an image of a Western blot showing that reduction of HS biosynthetic function prevents increases of ubiquitin-modified protein in the brains of ROS exposed animals. Accumulation of insoluble ubiquitinated particles (IUPs) was examined in the triton-X100 insoluble fraction of total head proteins. UAS-mCherry RNAi, an shRNAi with no predicted targets in the *Drosophila* genome, was used as a control. Overexpression of Atg8a (UAS-Atg8a) was used as a control for enhancement of autophagy. The UAS-constructs were expressed under control of elav-GAL4 with UAS-dcrII to enhance RNAi efficacy. Selected representative lanes from anti-ubiquitin stained membranes are shown in control vs. oxidant-exposed pairs. The ratio depicted over these images is the average density of anti-ubiquitin staining, normalized to loading, in (+) samples divided by (−) samples. (−) denotes the absence and (+) the presence of 2% H2O2 in the food medium.

In wild type animals, ROS exposure increased the level of ubiquitin-modification of brain proteins, while increasing autophagy by overexpression of Atg-8a reduced the levels of ubiquitin-modified proteins compared to control animals (FIG. 4). In adult flies expressing either of two unique RNAi constructs to knock down sfl expression, the levels of insoluble ubiquitin-modified proteins were similarly reduced in oxidant-exposed animals compared to controls. These findings show that the level of key genes required for heparan sulfate biosynthesis have an impact on ROS-mediated accumulation of ubiquitin-modified proteins in the brain.

Example 6 Knockdown of sfl or ttv Suppresses Neurodegeneration Mediated by Overexpression of Presenilin Reducing heparan sulfate biosynthetic function provided protection from ROS, extending survival to peroxide exposure. This enhanced survival was accompanied by reductions in ubiquitin-modified proteins in the brain, indicative of increased clearance of damaged proteins. The present investigators further explored whether reductions of heparan sulfate biosynthesis were protective for neurotoxic stress.

Missense mutations in Presenilins account for a sizable fraction of familial AD cases and models of Presenilin-mediated neurodegeneration have been established in *Drosophila*. Recent analysis of 138 pathogenic mutations in PSEN1 demonstrate that approximately 90% compromise the function of the encoded γ-secretase, further supporting the hypothesis that neuronal loss is likely a consequence of this reduced function. Overexpression of Presenilin in *Drosophila* produces apoptotic and neurogenic phenotypes resembling Presenilin loss-of-function phenotypes, indicating this model provides some parallels with the human pathology. Presenilin overexpression in the *Drosophila* retina produces neuronal loss and patterning abnormalities. This model was therefore employed to determine if downregulation of heparan sulfate biosynthesis could affect neuronal loss and disruption of retinal patterning mediated by overexpression of Psn.

Figures 5A, 5B, 5C, 5D:
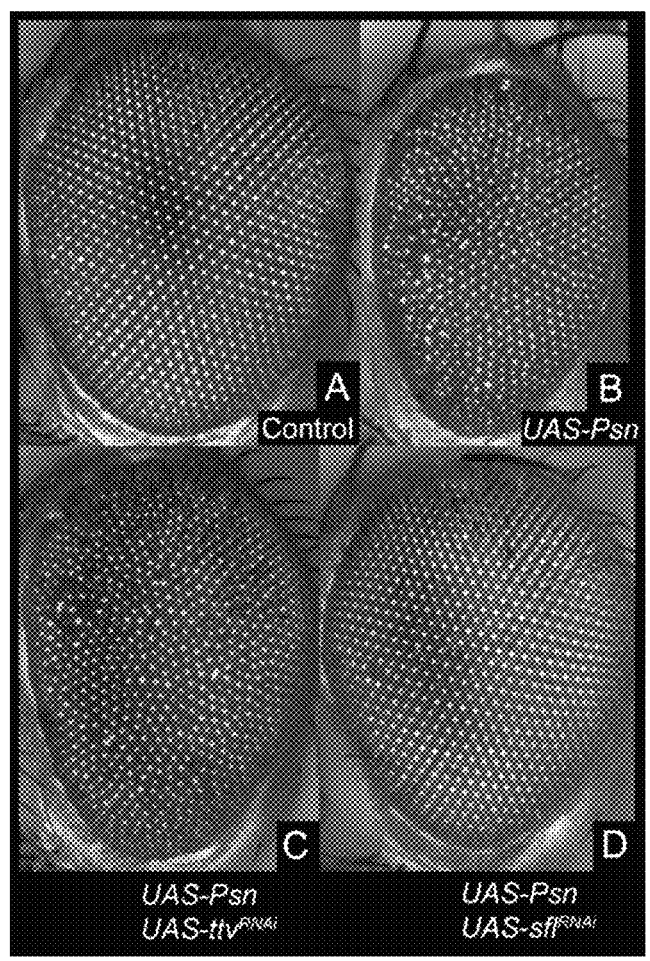
FIGS. 5A, 5B, 5C, 5D, 5E, and 5F show that reduction of sfl or ttv function rescues retinal abnormalities produced by overexpression of Presenilin. Transgene-mediated overexpression of Presenilin in neurons produces cell death and a reduction of the size of the eye, as well as disrupted patterning, evident as the relative positions of ommatidia, the photoreceptive units of the retina. Using brightfield illumination, serial optical sectioning and computational reconstruction, high-resolution images of the retina were obtained. Light reflection from each ommatidium provides the location and hence geometry of the photoreceptor units.
Figure 5E:
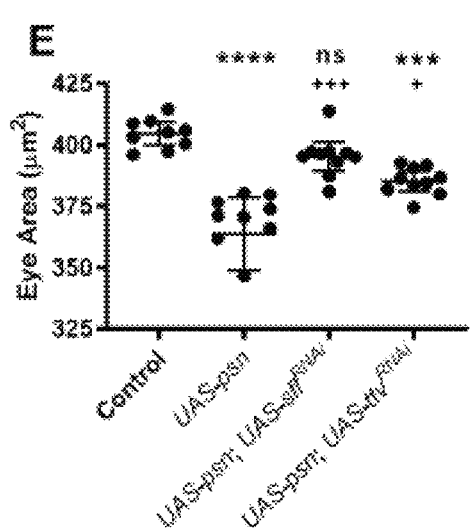
Figure 5F:
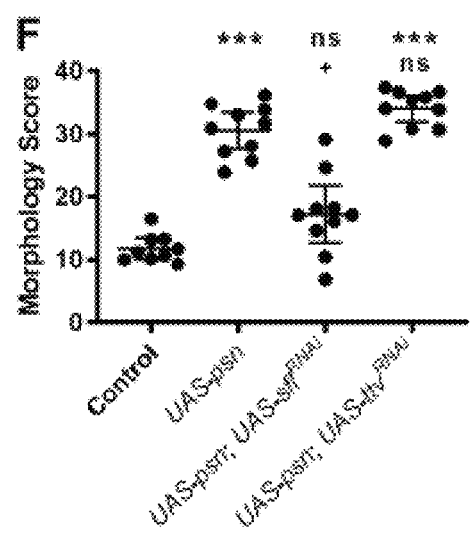

A *Drosophila* Psn transgene was expressed under the direction of a neuron-specific Gal4 line, in the presence or absence of UAS-transgenes encoding double-stranded RNAi targeting either ttv or sfl mRNAs. Expression of Psn produces a marked reduction in the size of the adult eye as well as a disruption of patterning, seen in the disorganization of the facets of the retina (FIG. 5, compare 5A and 5B). RNAi of sfl produced a significant rescue of both retinal size reduction and disordering (FIG. 5, A, B, D, E and F). The degree of patterning defect was measured using Flynotyper, an automated image processing algorithm that measures several features of retinal organization using the light reflected from each eye facet. Flynotyper calculates a single numerical score, reflecting several features of eye geometry, RNAi of ttv significantly rescued retinal size (FIG. 5C, 5E), represented as eye area, but did not improve the degree of retinal disorganization (FIG. 5F). Thus, compromising the function of two different genes in the heparan sulfate biosynthetic pathway reduced the developmental toxicity of Psn overexpression. These findings demonstrate that reducing heparan sulfate production is sufficient to protect cells from a neurotoxic and neuropatterning insult.

Example 7. Altering Heparan Sulfate Structure Rescues Muscle Degenerative Phenotypes of Parkin Mutants Autophagy is responsible for engulfment and removal of damaged mitochondria, a function critical for mitochondrial quality control. Mutations in parkin (park), a *Drosophila* homolog of the human Parkin-encoding gene (PARK2), have been identified and animals bearing these mutations characterized. Mutations in the human gene, PARK2, are responsible fir a substantial fraction of familial Parkinson's Disease patients, emphasizing the relevance of understanding PARK2/parkin function in the pathophysiology of this disorder. Park protein is a ubiquitin ligase responsible for the tagging of damaged mitochondria for autophagosome-lysosomal destruction.

Studies of Drosophila park mutants have demonstrated that Park affects mitochondrial surveillance and autophagy-mediated removal. Loss of park produces degeneration of flight muscle, a highly metabolically active cell, and certain allelic combinations of park (park$^1$/park$^{A21}$) survive to adulthood but are flightless, showing progressive muscle degeneration. Thus, the capacity of altering heparan sulfate biosynthesis to alter flight muscle cell degeneration in park mutants was investigated, with the rationale that increasing autophagy could ameliorate the accumulation of damaged mitochondria.

Figure 6A:
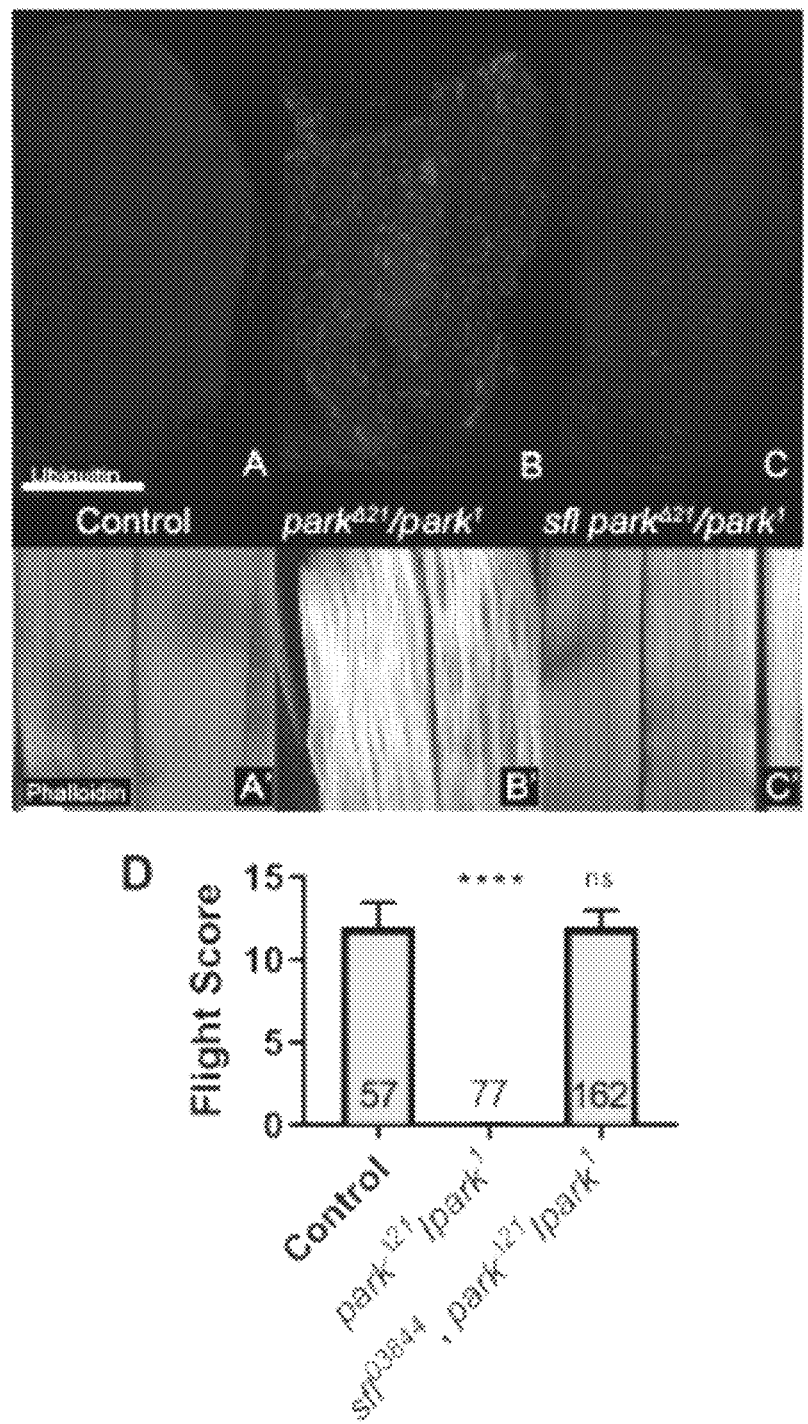
FIGS. 6A, 6A', 6B, 6B', 6C, 6C', and 6D show that reducing sfl function rescues muscle deficits found in parkin mutants. Animals homozygous for parkin alleles show flight muscle degeneration, accompanied by accumulation of ubiquitin and actin filament degeneration (compare FIGS. 6A and 6A' to 6B and 6B'). Note the accumulation of ubiquitin in parkΔ21/park1 animals compared to controls and the marked decrease in ubiquitin in animals bearing these same park alleles as well as a null allele of sfl (sfl03844 parkΔ21/park1).
Figures 7A, 7B, 7C:
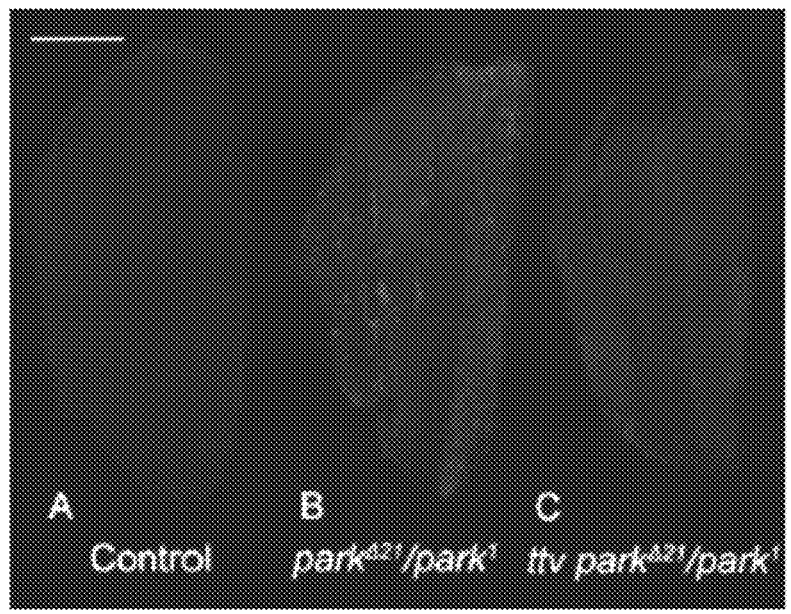
FIGS. 7A, 7B, and 7C are images showing that reduction of ttv function rescues flight muscle abnormalities of parkin mutant animals. For this comparison, adult flight muscles were dissected, fixed, stained with anti-ubiquitin antibody and visualized by confocal microscopy. parkΔ21/+ animals served as controls for this experiment. Note the reduced levels of anti-ubiquitin signal intensity in animals bearing a single allele of ttv (FIG. 7B versus FIG. 7C). The frequency distribution of anti ubiquitin signal (number of pixels for each pixel intensity level, see FIG. 11) was assessed for 15 animals of each genotype and analyzed using the Wilcoxon Signed Ranked Median Test. This assessment showed a significant difference ($p<0.005$) between parkΔ21/park1 and ttv00681; parkΔ21/park1 animals.
Figure 10:
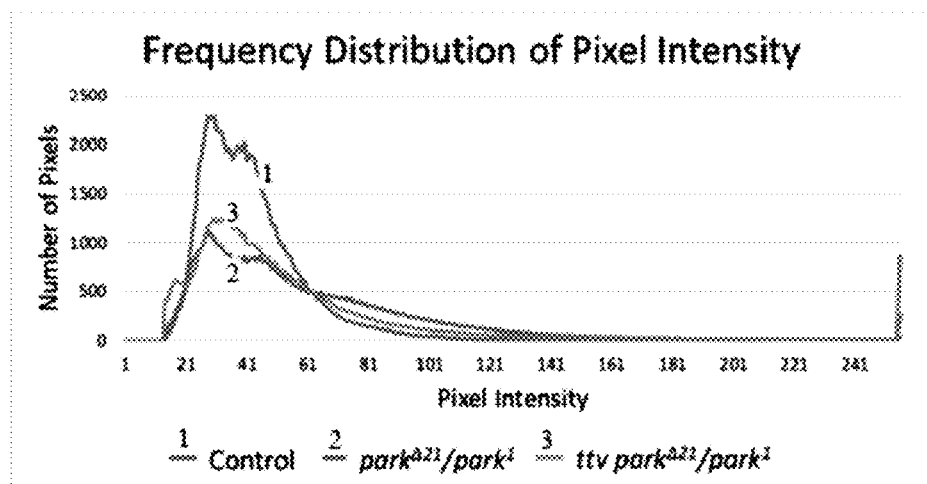
FIG. 10 is a graph showing frequency distribution of pixel intensities for anti-ubiquitin staining in flight muscles of parkin mutants and ttv/+; parkΔ21/park1 animals. The frequency plots represent the averages of three independent experiments, with n=15 for each genotype. Note that parkΔ21/park1 animals showed a shift, with more pixels with elevated brightness or intensity compared to controls (park1/+). The distribution of pixel intensities is shifted toward the control distribution when animals are heterozygous for ttv (ttv00681/+; parkΔ21/park1). The frequency distribution of parkΔ21/park1 is significantly different from ttv00681/+; parkΔ21/park1 (p<0.001, Wilcoxon Signed Ranked Median Test)

Heterozygosity for sfl had a profound effect and reduced the severity of park mutant phenotypes (FIG. 6) Both sfl$^{9B4}$ and sfl$^{03844}$ alleles had similar effects on suppressing muscle cell abnormalities, including the accumulation of ubiquitin-modified proteins and disordering of actin filaments. Muscle function was evaluated with an assay that provides a quantitative assessment of flight. park$^1$/park$^{A21}$ animals are incapable of flight (zero score) whereas sfl park$^1$/park$^{A21}$ flies have near wild type levels (FIG. 6D). Similar analyses were conducted for interactions between ttv and park and heterozygosity for a null allele of ttv also showed significant rescue of park$^1$/park$^{A21}$ flight muscle abnormalities (FIG. 7). Reduction of ttv function also reduced the levels of ubiquitin-modified proteins in the indirect flight muscle of park mutants (FIG. 7 and FIG. 10). Quantitative PCR was used to confirm that mutations in sf ttv and park (park$^{A21}$) reduced the respective levels of mRNA (FIG. 11) and predicted levels of mRNA were found in the animals that showed rescue of park-mediated phenotypes. The rescue of park mutant animals by reductions of sfl or ttv function provides evidence of the capacity of altered heparan sulfate synthesis to promote cellular repair systems that counteract cellular stresses, including accumulation of damaged mitochondria.

Figures 8A, 8B, 8C:
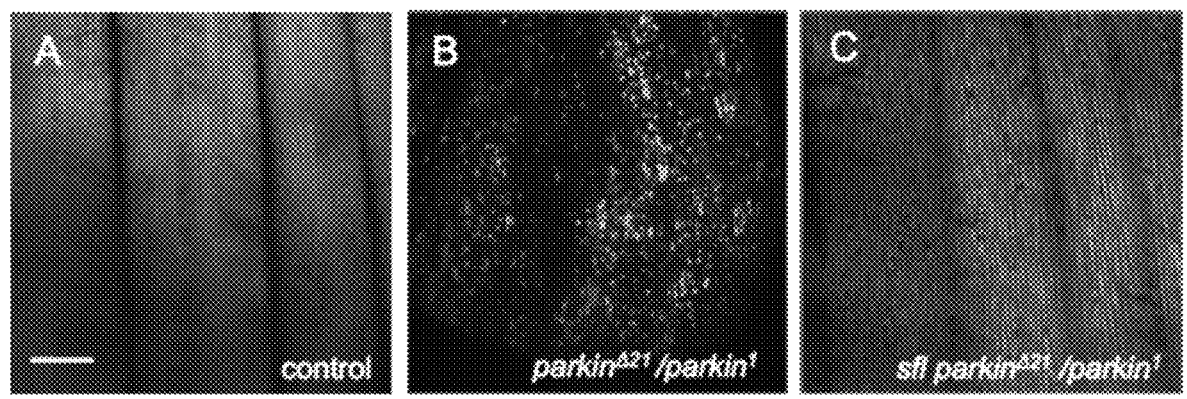
FIGS. 8A, 8B, and 8C are images showing that reducing sfl function rescued mitochondrial abnormalities of parkin mutants. Mitochondria in adult flight muscle cells were tagged with UAS-mitoGFP expressed in muscle under the direction of a muscle-specific Gal4 line, mef2-Gal4. This marker was crossed into parkin mutants and parkin mutants bearing a single mutant allele of sfl. Representative images from two separate experiments are shown (n=52). The scale bar represents 30 μM.

Parkin functions in the surveillance and tagging of damaged mitochondria for removal by autophagic degradation. This is achieved via Parkin mediated ubiquitin-modification of outer membrane mitochondrial proteins, providing a molecular tag for recognition by the autophagy machinery. In accordance with the function of Parkin in mitochondrial surveillance, parkin mutants show accumulations of abnormal mitochondria. To determine if this critical and central phenotype of parkin mutants is affected by the levels sfl function, animals were examined wherein mitochondria were selective tagged by the expression of mito-GFP, a mitochondrial, targeted protein, under the direction of a muscle-specific Gal4 line, mef2-Gal4. parkin mutants showed large and dysmorphic mitochondria compared to control animals and these changes were reversed by heterozygosity for sfl (compare FIG. 8A to FIGS. 8B and 8C). These results establish that changes in heparan sulfate structure can modulate the cellular pathology of parkin mutants at the level of the primary deficit, failure to tag and removed damaged mitochondria.

Reducing the gene dosage of sfl had a remarkable capacity to rescue muscle cell death mediated by park mutations, affecting actin morphology, accumulation of ubiquitin, and dysmorphology of mitochondria, as well as the key measure of flight muscle function, the capacity to fly. Reductions of ttv function also rescued muscle abnormalities of park mutants. These in vivo interactions demonstrate the capacity of heparan sulfite levels and structure to rescue cell degeneration in a model of a human neurodegenerative disorder.

Figures 9A, 9B:
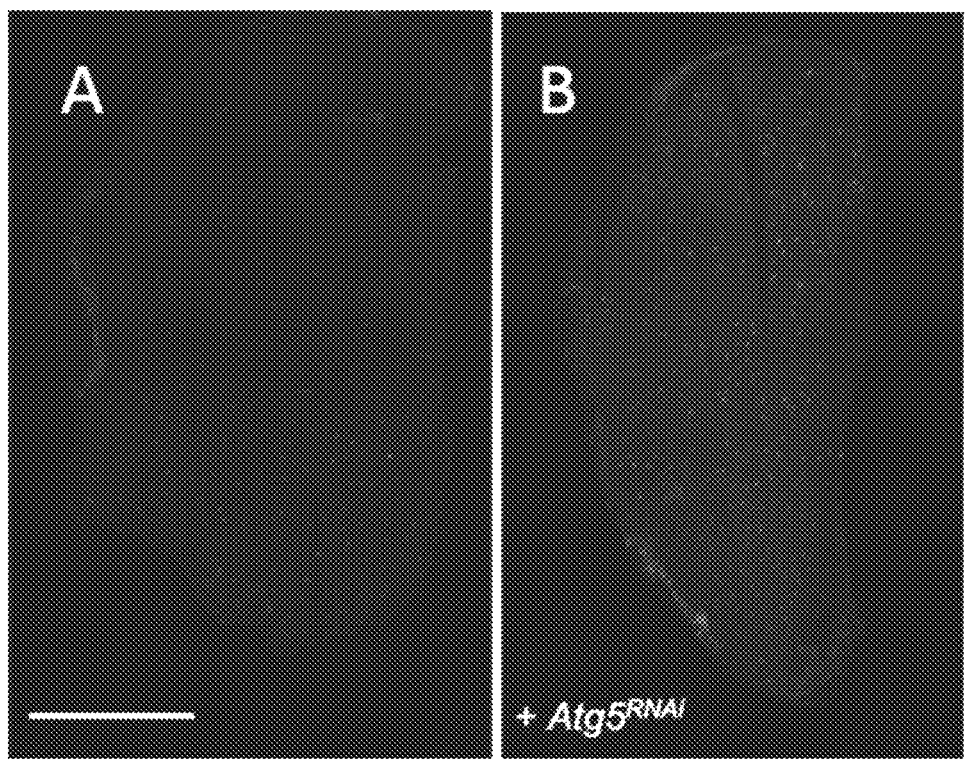
FIGS. 9A and 9B are images demonstrating autophagy dependence of sfl-mediated rescue of parkin flight muscle ubiquitin accumulation. RNAi of a critical autophagy gene, Atg5, resulted in increased intracellular ubiquitin, a hallmark of the cellular pathology observed in parkΔ21/park1 flight muscles; a phenotype which is rescued by sfl (see FIG. 6). The number of ubiquitin-positive punctae/pixel were measured and determined to be significantly different between these two groups using a two-tailed t-test statistic [t=6.49, $p<0.0001$, n=32]. Scale bars represent 200 μM.

Example 8. Autophagy Dependence of sfl-Mediated Rescue of Cell Degeneration in Parkin Mutants Alteration of heparan sulfate structure has a dramatic impact in two genetic; models of cell degeneration in Drosophila, overexpression of Presenilin and parkin mutants. It is also evident that heparan sulfate structure can modulate autophagy in muscle, fat body, and neurons. To determine if autophagy function is required for the capacity of sfl to affect the rescue of cell degeneration in parkin mutants, muscle-directed expression (mef2-Gal4) of Atg5$^{RNAi}$ was employed. In parkin mutant animals, ubiquitin accumulation is reduced by the presence of a single sfl mutant allele (FIG. 6). When reared at 25° C., a temperature where Gal4-directed transcription is active, RNAi of Atg5 resulted in significantly increased accumulation of ubiquitin in the muscle cells of sfl park$^{A21}$/mef2-Gal4 park$^1$ adult animals (FIG. 9). At this temperature, the knockdown of Atg5 produced significant lethality in sfl park$^{A21}$/mef2-Gal4 park$^1$ animals. A replicate experiment at 23° C., where Gal4 activity, and hence the degree of RNAi, was lower, reduced the lethality and also showed significant increases in ubiquitin positive punctae in Atg5$^{RNAi}$ bearing animals, although the punctae were fewer and less bright (west, p=0.01). The elevated levels of punctae required both parkin alleles to be present. These findings demonstrate that an intact autophagy system is required for the full rescue of parkin mutants mediated by reductions in sfl function.

Figure 12:
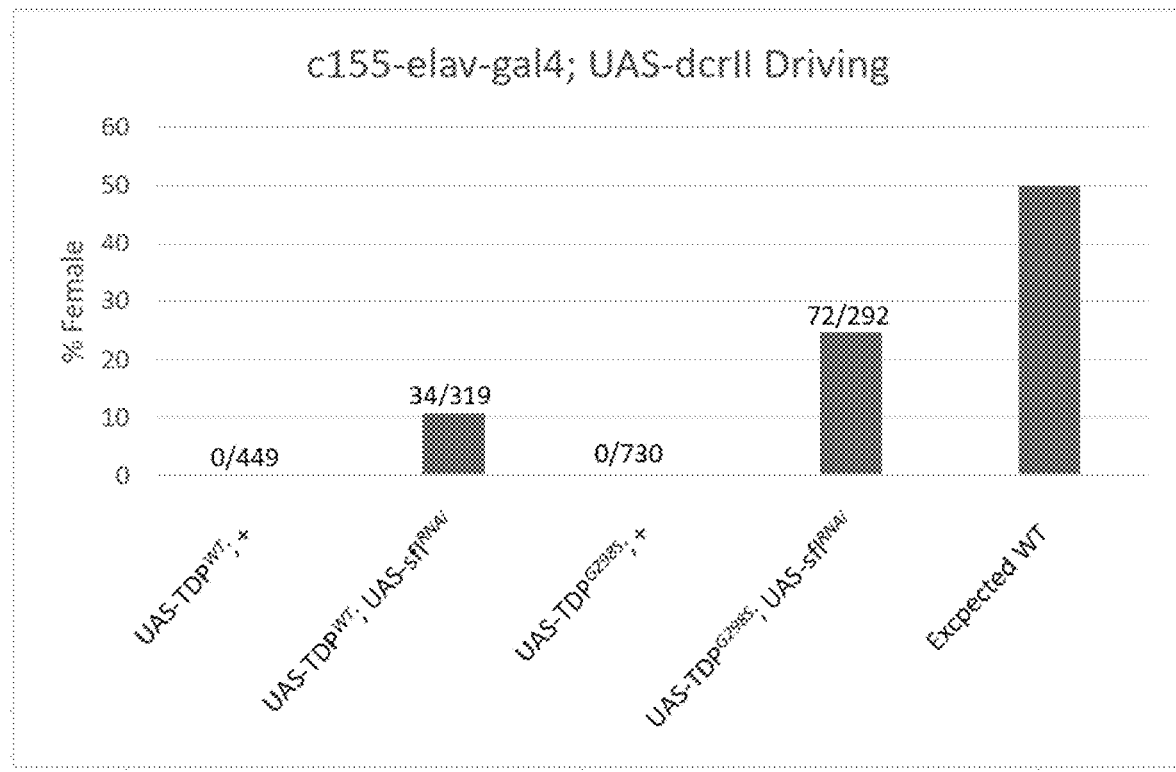
FIG. 12 is a graph showing rescue of lethality produced by expression of human TDP-43 in the central nervous system by knockdown of sfl using an RNAi construct. Two different forms of TDP-43 were expressed in neurons using the elav-Gal4 transonic, a neuron expressed transcriptional activator, that directs expression of UAS-TDP constructs as well as an RNAi transgene directed at the sfl gene, the fly homolog of vertebrate Ndst-encoding genes. Note that expression of sflRNAi rescues the lethality of animals expressing either of the two forms of human TDP-43. In this experiment, only female animals receive the elav-Gal4 transgene. Hence, the effect of the TDP-43 and sflRNAi transgenes governs the percentage of female flies that survive to adulthood.
Figure 15A:
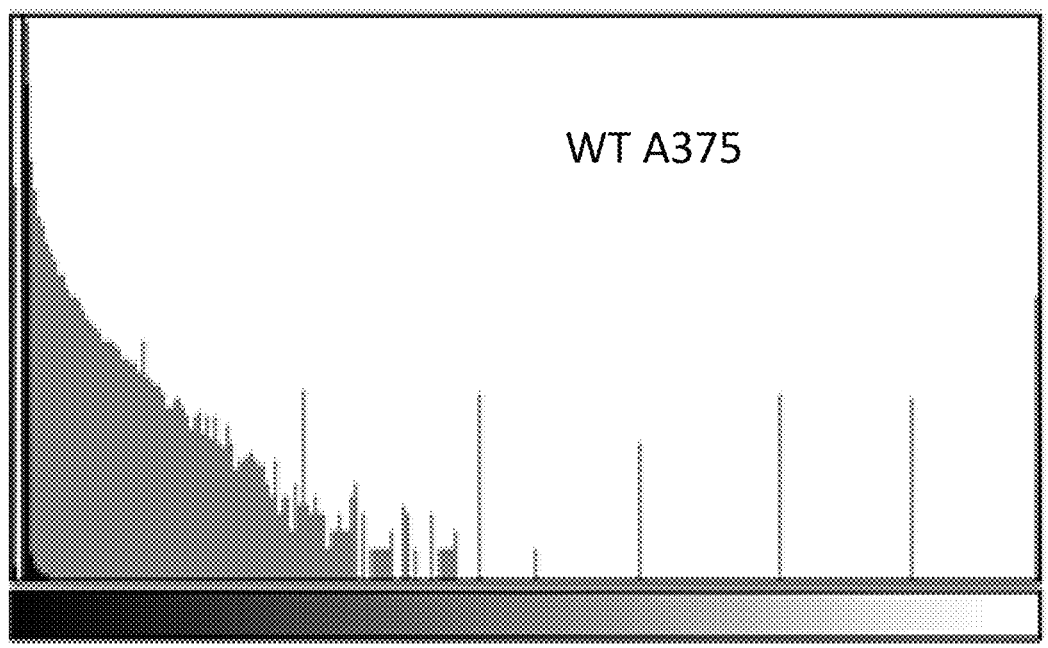
FIG. 15A is a graph showing pixel frequency distribution (number of pixels on Y axis, brightness on X axis) for wild-type (WI) human A375 cells stained with the fluorescent vital dye, CytoID (Enzo labs), that specifically tags autophagosomes.
Figure 15B:
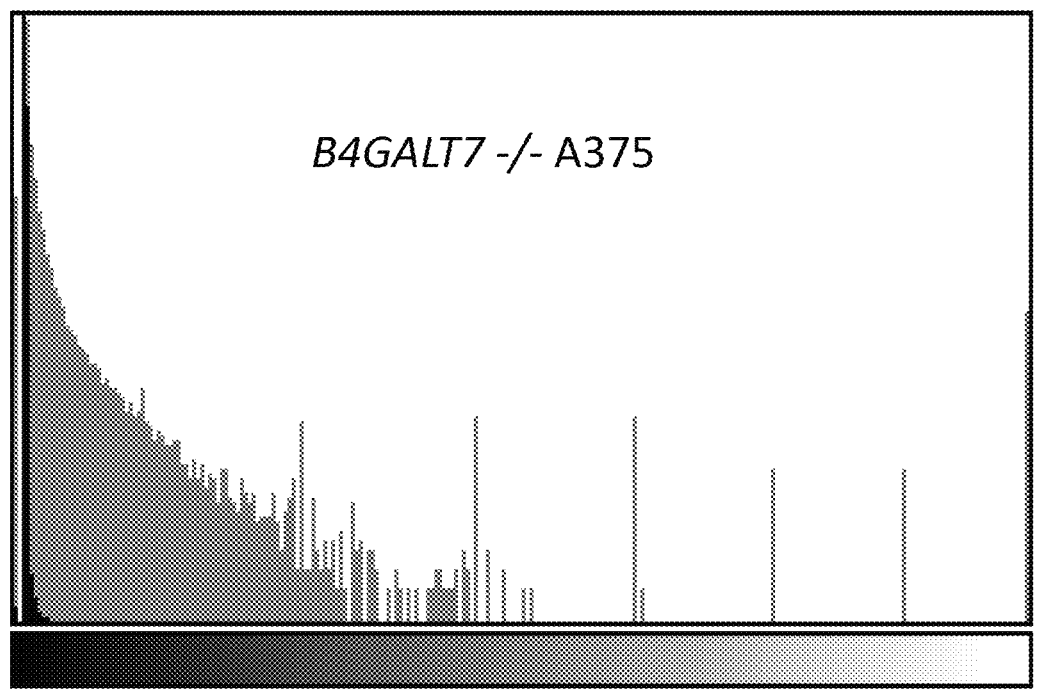
FIG. 15B is a graph showing pixel frequency distribution (number of pixels on Y axis, brightness on X axis) for B4GALT7-/- human A375 cells stained with the fluorescent vital dye, CytoID, that specifically tags autophagosomes.
Figure 15C:
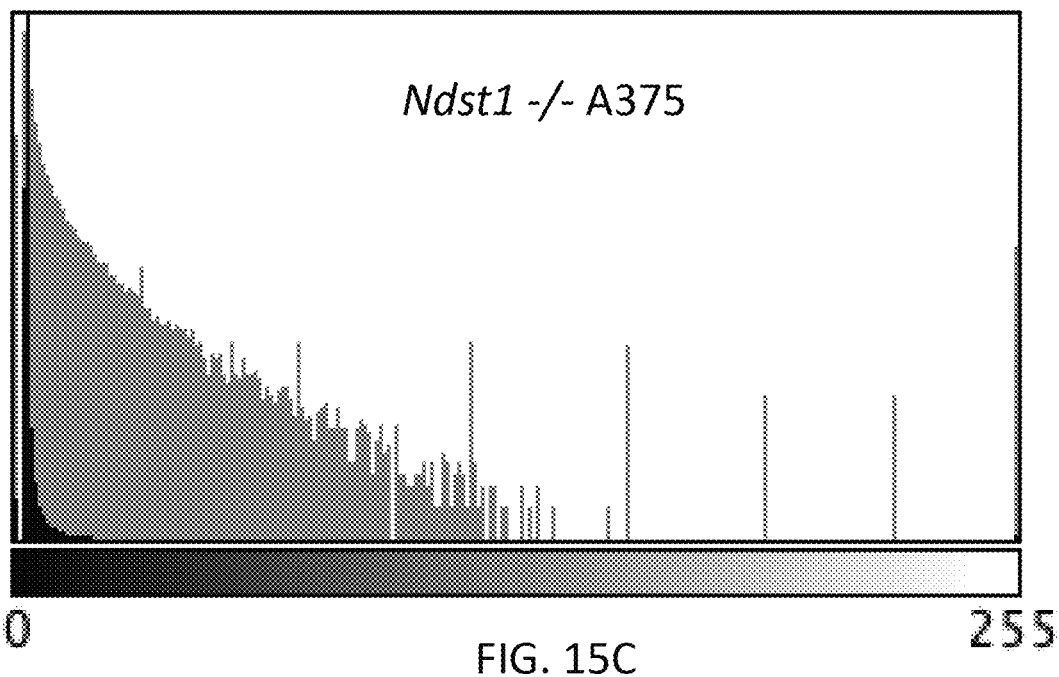
FIG. 15C is a graph showing pixel frequency distribution (number of pixels on Y axis, brightness on X axis) for NDST-/- human A375 cells stained with the fluorescent vital dye, CytoID, that specifically tags autophagosomes.
Figure 15D:
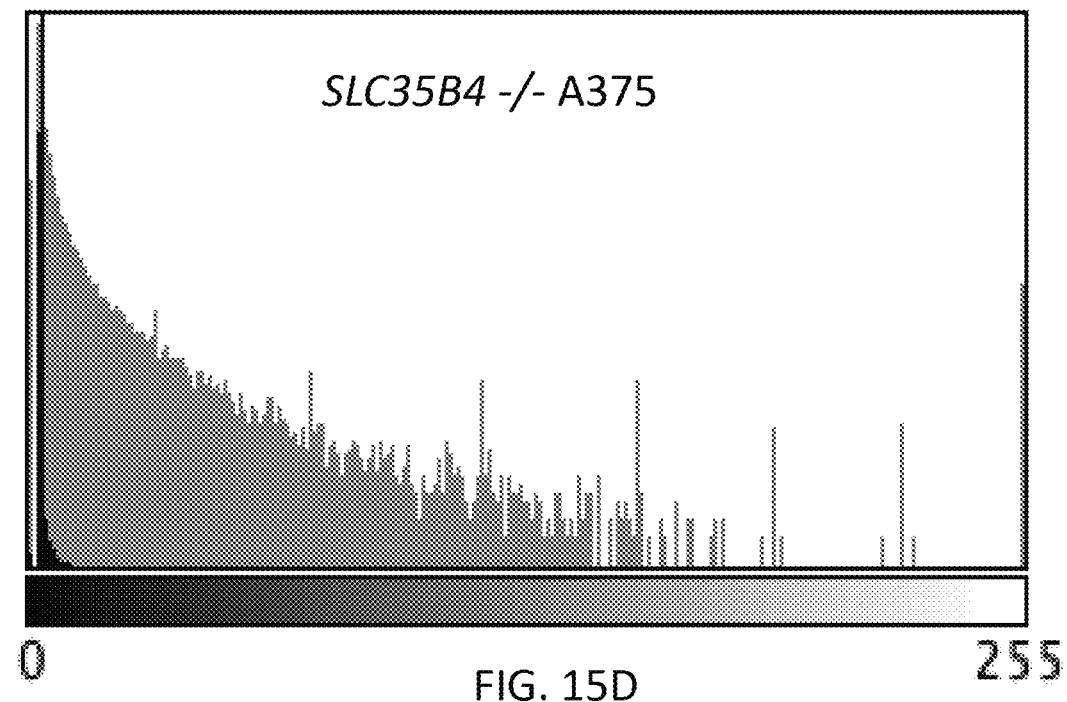
FIG. 15D is a graph showing pixel frequency distribution (number of pixels on Y axis, brightness on X axis) for SLS35B4-/- human A375 cells stained with the fluorescent vital dye, CytoID, that specifically tags autophagosomes; Each of FIGS. 15A, 15B, 15C, and 15D was generated from an equal size field of cells at equal density. Note the greater representation of brighter pixels in SLC35B4 and Ndst-/- cells compared to wild type and B4GALT7-/- cells.

Example 9. Amyotrophic Lateral Sclerosis (ALS) Model: Lethality of Expression of Human TDP-43 in the CNS by Knockdown of sfl using an RNAi Construct Two different forms of TDP-43 were expressed in neurons using the elav-Gal4 transgene: (1) a neuron expressed transcriptional activator that directs expression of UAS-TDP constructs, and (2) an RNAi transgene directed at the sfl gene, the fly homolog of vertebrate Ndst-encoding genes. Results showed that expression of sfl$^{RNAi}$ rescues the lethality of animals expressing either of the two forms of human TDP-43 (FIG. 12). In this experiment, only female animals receive the elav-Gal4 transgene. Hence, the effect of the TDP-43 and sfl$^{RNAi}$ transgenes governs the percentage of female flies that survive to adulthood.

Example 10. Heparan Sulfate Biosynthesis Affects Autophagy and Lysosomal Trafficking in Human Cells In this example, it was determined directly that heparan sulfate modified protein-mediated modulation of autophagy and mitophagy occurs in human cells. A human melanoma cell line, A375, was used where CRISPR/Cas9 technology has been employed to generate mutations in a number of specific genes required for heparan sulfate biosynthesis and modification (described in detail in Poli, M., E. K. F. Anower, M. Asperti, P. Ruzzenenti, M. Gryzik et al., 2019. Hepatic heparan sulfate is a master regulator of hepcidin expression and iron homeostasis in human hepatocytes and mice. J Biol Chem 294 (36):13292-13303. In this human cell line, an autophagy and a lysosomal marker was evaluated in parental A375 cells compared to Ndst1-/- mutants. These studies showed significant increases in both autophagosomes and lysosomes under baseline growth conditions in the Ndst1-/- cells (compare FIG. 13A with FIG. 13B), as well as accentuated responses upon induction of autophagy by rapamycin treatment, a Tor inhibitor and autophagy inducer (compare FIG. 14A with FIG. 14B).

A375 cells with mutations in other key heparan sulfate biosynthetic genes have provided the means of determining some of the structural requirements of this response. SLC35B4 encodes a transporter for the high energy sulfate donor, phosphoadenosine-5'-phosphosulfate (PAPS), required for all sulfation steps in the Golgi apparatus. PAPS is synthesized in the cytoplasm and transported into the Golgi where is provides the sulfate donor required for sulfation of heparan sulfate and other molecules. Cells with mutations in B4GALT7 were also generated with CRISPR/Cas9 technology. B4GALT7 encodes a galactosyl transferase required for the synthesis of the tetrasaccharide linker found in all glycosaminoglycans that serves to connect the clycoaminoglycan chain to the peptide backbone of the modified protein. Knockout of B4GALT7 eliminates all glycosaminoglycan biosynthesis. Interestingly, basal levels of autophagosomes are highest in SLC35B4−/− cells, followed by Ndst−/−. Levels of basal autophagy in B4GALT7−/− cells do not appear different from the wild type A375 cells (see FIGS. 15A-D). These findings indicate that the sulfation state of heparan sulfate is critical for determining basal autophagy levels, but complete absence of glycoaminoglycans does not appreciably trigger the response. Thus an undersulfated heparan sulfate chain appears to be critical to activate increased basal autophagy. These findings also establish the capacity of heparan sulfate structure and sulfation state to regulate autophagy and membrane trafficking in human cells.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A method of identifying a modulator of autophagy, the method comprising:
   administering a test substance to a cell, the cell comprising an N-deacetylase N-sulfotransferase (NDST) polypeptide and a substrate for NDST, under reaction conditions that promote specific interaction between the NDST polypeptide and the substrate for NDST, detecting a change in enzymatic activity of the NDST polypeptide, and
   detecting a corresponding change in autophagy in the cell, thereby identifying the test substance as a modulator of autophagy.

2. The method of claim 1, wherein the NDST substrate is N-acetylglucosamine (GlcNAc).

3. The method of claim 1, wherein detecting a change in enzymatic activity of the NDST polypeptide comprises detecting a change in specific interaction between the NDST polypeptide and the substrate for NDST.

4. The method of claim 1, wherein detecting a change in enzymatic activity of the NDST polypeptide comprises detecting a change in deacetylation of GlcNAc and/or detecting a change in formation of N-sulfo glucosamine (GlcNS).

5. The method of claim 1, wherein detecting a change in enzymatic activity of the NDST polypeptide comprises detecting a change in formation of heparan sulfate.

6. The method of claim 1, further comprising comparing the specific interaction between the NDST polypeptide treated with the test substance and the NDST substrate with a control.

7. The method of claim 6, wherein the control comprises specific interaction between the NDST polypeptide and the NDST substrate in the absence of the test substance.

8. The method of claim 1, wherein the test substance comprises a nucleic acid.

9. The method of claim 1, wherein the test substance is a small molecule organic or inorganic inhibitor of NDST.

10. The method of claim 8, wherein the test substance is selected from the group consisting of: an antisense molecule, an aptamer, siRNA, shRNA, miRNA, a DNAzyme, and a ribozyme.

11. The method of claim 1, wherein the test substance comprises a protein.

12. The method of claim 1, wherein the test substance comprises a carbohydrate.

13. The method of claim 1, wherein the test substance comprises a lipid.

14. The method of claim 1, wherein the test substance comprises an antibody.

15. The method of claim 1, wherein the test substance comprises a decoy agent.

* * * * *